(12) United States Patent
Kohda et al.

(10) Patent No.: US 8,361,752 B2
(45) Date of Patent: Jan. 29, 2013

(54) ARTIFICIAL SCAFFOLDING MATERIAL FOR PROTEIN RETENTION AND USE OF THE SAME

(75) Inventors: Katsunori Kohda, Nisshin (JP); Katsuhiro Ohno, Aichi-gun (JP); Takao Imaeda, Nisshin (JP); Kazuo Sakka, Tsu (JP)

(73) Assignees: Kabushiki Kaisha Toyota Chuo Kenkyusho, Aichi-Gun (JP); Mie University, Tsu-Shi (JP)

( * ) Notice: Subject to any disclaimer, the term of this patent is extended or adjusted under 35 U.S.C. 154(b) by 1128 days.

(21) Appl. No.: 12/219,911

(22) Filed: Jul. 30, 2008

(65) Prior Publication Data
US 2009/0035811 A1 Feb. 5, 2009

(30) Foreign Application Priority Data

Jul. 31, 2007 (JP) ................................ 2007-199513
Nov. 20, 2007 (JP) ................................ 2007-301038

(51) Int. Cl.
C12P 1/00 (2006.01)
C12P 21/04 (2006.01)
C12N 15/00 (2006.01)

(52) U.S. Cl. ........................... 435/71.1; 435/41; 435/440
(58) Field of Classification Search ........................ None
See application file for complete search history.

(56) References Cited

U.S. PATENT DOCUMENTS

2010/0204445 A1 8/2010 Ishikawa et al.
2011/0250668 A1 10/2011 Suzuki et al.

FOREIGN PATENT DOCUMENTS

| JP | A-2004-236504 | 8/2004 |
| JP | A-2000-157282 | 6/2008 |
| WO | WO 2009/028531 A1 | 3/2009 |
| WO | WO 2010/016067 A2 | 2/2010 |

OTHER PUBLICATIONS

Perret et al. "Use of antisense RNA to modify the composition of cellulosomes produced by *Clostridium cellulolyticum*" Molecular Microbiology (2004) 51 (2), 599-607.*
Desvaux "The cellulosome of *Clostridium cellulolyticum*" Enzyme and Microbial Technology 37 (2005) 373-385.*
Pages et al. "Sequence Analysis of Scaffolding Protein CipC and ORFXp, a New Cohesin-Containing Protein in *Clostridium cellulolyticum*: Comparison of Various Cohesin Domains and Subcellular Localization of ORFXp" Journal of Bacteriology, Mar. 1999, p. 1801-1810, vol. 181, No. 6.*
S. Perret, L. Casalot et al., J. Bacterol.; Production of Heterologous and Chimeric Scaffolins by *Clostridium acetobutylicum* ATCC 824; Journal of Bacteriology; 186(1)253-257 (2004).
Junji Ito et al., Development of Immobilization Method for Protein to Cell Surface of Yeast via Binding Between Proteins; C106, SCE 71st Annual Meeting (Tokyo, 2006).
Arnold L. Demain et al., "Cellulase, Clostridia, and Ethanol," *Microbiology and Molecular Biology Reviews*, 2005, pp. 124-154, vol. 69-1.
Roy H. Doi et al., "Cellulosomes from Mesophilic Bacteria," *Journal of Bacteriology*, 2003, pp. 5907-5914, vol. 185-20.
Apr. 13, 2012 Japanese Office Action issued in Japanese Application No. 2010-088952 (with partial English-language Translation), 6 pgs.
Annette Herscovics et al., "Glycoprotein Biosynthesis in Yeast," FASEB, 7, pp. 540-550, 1993.
Jun. 12, 2012 Office Action issued in Japanese Patent Application No. 2008-198497 (with translation), 7 pgs.
Bayer, Edward et al., "The cellulosome-a treasure-trove for biotechnology", *Trends Biotechnol.*, 1994, 12 [9], pp. 379-386.
Ohmiya, Kunio, "Analysis of a Nano Arrangement of Cellulase Complex and Construction of an Artificial Enzyme Complex for Converting $CO_2$ to Methanol," *Wave Mie University*, 2004, [30], pp. 13-14 (with translation).
Karpol et al., "Functional asymmetry in cohesin binding belies inherent symmetry of the dockerin module: insight into cellulosome assembly revealed by systematic mutagenesis," *Biochem. J.*, 2008, pp. 331-338, vol. 410, Great Britain.
Carvalho et al.,"Evidence for a dual binding mode of dockerin modules to cohesins," *PNAS*, 2007, pp. 3089-3094, vol. 104, No. 9.
Mechaly et al., "Cohesin-Dockerin Interaction in Cellulosome Assembly," *The Journal of Biological Chemistry*, 2001, pp. 9883-9888, vol. 276, No. 13, United States.

* cited by examiner

*Primary Examiner* — Jon P Weber
*Assistant Examiner* — Thane Underdahl
(74) *Attorney, Agent, or Firm* — Oliff & Berridge, PLC

(57) ABSTRACT

The present invention provides an artificial scaffolding material for retaining proteins suitable for placing contiguously one species or two or more species of proteins such as enzymes. To this end, the artificial scaffolding material for retaining proteins is provided with a cell and scaffolding proteins heterologous to the cell and placed on the surface layer side of the cell at an extent that allows aggregation properties to be conferred to the cell, and provided with a plurality of non-covalently binding protein-binding domains arranged in tandem.

34 Claims, 16 Drawing Sheets

STRUCTURE OF CipA GENE

NO DISPLAY   TypeII COHESIN
Histag ANTIBODY   Histag ANTIBODY

TYPE II COHESIN ONLY (ANTI-Xpress ANTIBODY)    TYPE II COHESIN + CBD-Coh-DoCII (ANTI-Xpress ANTIBODY)    TYPE II COHESIN + CBD-Coh-Coh-DoCII (ANTI-Xpress ANTIBODY)

ARTIFICIAL SCAFFOLDING MATERIAL FOR PROTEIN RETENTION AND USE OF THE SAME

CROSS-REFERENCE TO RELATED APPLICATION

This application claims priority to Japanese Patent Applications No. 2007-301038, filed on Nov. 20, 2007 and No. 2007-199513, filed on Jul. 31, 2007, the contents of which are hereby incorporated by reference into the present application.

BACKGROUND OF THE INVENTION

1. Field of the Invention

The present invention relates to artificial scaffolding material for retaining protein and use of the same, and more particularly, to artificial scaffolding material suitable for causing a plurality of species of proteins such as enzymes to function cooperatively or stepwise, and the use of the same.

2. Description of the Related Art

In general, to carry forward a series of reactions via cooperative or stepwise reactions of a plurality of enzymes, it is thought to be preferable that related enzymes are arranged in a given order.

For instance, to degrade and use a biological integrative structure such as cellulose, cooperative and stepwise reactions of a plurality of enzymes are necessary. A microorganism species that degrades cellulose is provided with a complex of multiple species of enzymes (cellulosome) for degrading cellulose, on the cell surface. A cellulosome is thought to effectively degrade crystalline cellulose that has a low-degradability, by being provided with a cellulose-binding protein that is bound by a plurality of cellulolytic enzymes.

Based on this knowledge, attempts have been made to artificially construct an enzymatic series with excellent reaction efficiency, by imitating the structure of a cellulosome and functionally arranging enzymes. For instance, a plurality of enzymes that use a cellulose-binding protein having a plurality of enzyme-binding domains derived from *Clostridium josui* or the like is disclosed (Japanese Patent Application Publication No. 2000-157282 and Japanese Patent Application Publication No. 2004-236504).

In addition, a technique in which mini-cellulosomes are secreted by *Clostridium acetobutylicum* is disclosed (S. Perret et al., J. Bacterol., 186 (1), 253-257 (2004)). Furthermore, there also is an attempt of connecting to the surface layer of yeast cell a protein that comprises a cohesin derived from *Clostridium cellulovorans* and a ZZ domain derived from *Staphylococcus aureus* of which are connected by a linker (Itoh et al., C106, Proceedings of the 71th Meeting of Society of Chemical Engineers, Japan (2006)).

However, according to the above prior art references, although enzymes can be arranged using a linear scaffolding protein, they do not necessarily allow these enzymes to be arranged at high density. In addition, since the technique of the above S. Perret et al. produces mini-cellulosomes that use a linear scaffolding protein by secretion outside the cell, it is difficult to have the enzymes exist with a high contact probability with respect to substrate. In addition, although the technique of the above Itoh et al. surface layer-displays a linear scaffolding protein using agglutinin, the high degree of accumulation of the scaffolding protein at the cell surface layer cannot be achieved.

Thus, all of the above prior techniques handled the individual linear scaffolding protein provided with a plurality of protein binding sites, in forms that are separately secreted or displayed on the cell surface layer. Moreover, the above patent references and Itoh et al. intended to control the placement focusing on the functional arrangement of a plurality of enzymes. With Itoh et al., although a plurality of species of enzymes can be bonded to a scaffolding protein, the placement of scaffolding proteins in the cell surface layer cannot be controlled.

Therefore, in the current situation, no artificial scaffold has been provided yet, in which a plurality of proteins such as enzymes are placed at a high density to effectively degrade a substrate by cooperative or stepwise action of these proteins. In addition, no artificial scaffolding material has been provided yet, in which linear scaffolding proteins are placed two-dimensionally. In addition, no protein complex material has been provided, which has been complexed using such artificial scaffolding materials.

BRIEF SUMMARY OF THE INVENTION

An object of the present invention is to provide an artificial scaffolding material for retaining proteins, suitable for contiguously placing one species, or two or more species of proteins such as enzymes. Another object of the present invention is to provide an artificial scaffolding material suitable for placing proteins two-dimensionally. Moreover, another object of the present invention is to provide a protein complex material in which one species, or two or more species of proteins are placed contiguously or two-dimensionally. Furthermore, another object of the present invention is to provide a method for degrading cellulose using such protein complex material and a method for producing useful substance.

In order to obtain an artificial scaffolding material that readily allows a plurality of species of enzymes to be placed contiguously, which is one of the object matter of the present invention as described above, the present inventors attempted the development of a method for placing contiguously scaffolding proteins that are assumed to adopt a linear structure.

As a result of various tests, the present inventors discovered that a cell provided with scaffolding proteins that are provided with protein-binding domains in tandem on a surface layer of the cell itself had the tendency to express aggregation properties when provided with a given number or more of the protein-binding domains. The present inventors assumed that the expression of aggregation properties was due to these scaffolding proteins being placed not sparsely but contiguously.

Furthermore, with the scaffolding protein provided, with the protein-binding domains serving as a first scaffolding protein, and a second scaffolding protein provided with a binding domain with respect to the first scaffolding protein (scaffolding protein-binding domain) was prepared on the cell surface layer, the present inventors discovered that the first scaffolding protein could be bound to a scaffolding protein-binding domain of the second scaffolding protein. If the scaffolding protein-binding domains could be retained in tandem in the second scaffolding protein, the first scaffolding protein could be arranged two-dimensionally on the cell surface layer. Based on these observations, the present inventors completed the following inventions.

According to the technique taught in the present specification, an artificial scaffolding material for retaining proteins is provided. The artificial scaffolding material of the present technique is provided with a cell and first scaffolding proteins. The first scaffolding proteins are heterologous to the cell, and provided with a plurality of protein-binding domains that is capable of non-covalently binding and arranged in tandem, and placed on a surface layer side of the cell at an extent that allows aggregation properties to be conferred to the cell. At least one of the protein-binding domains may be a Type I cohesin domain of the Type I scaffolding protein of cellulosome.

At least one of the first scaffolding proteins may contain a cellulose-binding domain. The scaffolding proteins may be a Type I scaffolding proteins of a cellulosome or a variant of such Type I scaffolding proteins. The scaffolding proteins may be a Type I scaffolding proteins of cellulosome from *Clostridium thermocellum* or a variant of such Type I scaffolding proteins.

In addition, the first scaffolding proteins may be provided with three or more of the protein-binding domains. Alternatively, the first scaffolding proteins may be provided with four or more but seven or less of the protein-binding domains. Furthermore, the cell may express the first scaffolding proteins.

The artificial scaffolding material of the present invention may further be provided with a second scaffolding protein, which is heterologous to the cell. The second scaffolding protein has a plurality of scaffolding protein-binding domains that each can bind the respective first scaffolding proteins, via a non-covalent bond. The second scaffolding protein is placed on the surface layer of the cell, and each of the first scaffolding proteins has an interaction domain that can bind to one of the scaffolding protein-binding domains of the second scaffolding protein via a non-covalent bond. That is, the interaction domains may be bound to the scaffolding protein-binding domains.

In this artificial scaffolding material, the second scaffolding protein may be bound to the surface layer of the cell via a covalent bond. In addition, it may have a plurality of the scaffolding protein-binding domains in tandem. The scaffolding protein-binding domains may include the Type II cohesin domain of a Type II scaffolding protein of cellulosome. In addition, the second scaffolding protein may be a Type II scaffolding protein derived from a cellulosome or a variant of the Type II scaffolding protein. Further in addition, the second scaffolding protein may be a Type II scaffolding protein of cellulosome from *Clostridium thermocellum* or a variant of the Type II scaffolding protein. In addition, in this artificial scaffolding material, the cell may express the second scaffolding protein.

In any of the above artificial scaffolding materials of the present invention, the proteins may be enzymes. In addition, the enzymes may be selected from an enzyme group that degrades cellulose. In addition, the cell may be a microorganism, and may alternatively be yeast. In addition, the yeast may be alcohol-producing yeast or organic acid-producing yeast.

According to the present technique, a protein complex material is provided with: a cell; first scaffolding proteins that are heterologous to the cell and have a plurality of non-covalently binding protein-binding domains arranged in tandem and are placed on the surface layer side of the cell contiguously to one another, and one species or two or more species of proteins bound to the protein-binding domains via a non-covalent bond. In this complex material, a second scaffolding protein may further be provided. The second scaffolding protein is heterologous to the cell, has a scaffolding protein-binding domain that binds to the first scaffolding protein via a non-covalent bond, and is placed on the surface layer of the cell. Each of the first scaffolding proteins has an interaction domain that binds to the scaffolding protein-binding domain of the second scaffolding protein via a non-covalent bond, and this interaction domain may be bound to respective scaffolding protein-binding domain.

In this complex material, the second scaffolding protein may be bound to the surface layer of the cell via a covalent bond, and the second scaffolding protein may have a plurality of the scaffolding protein-binding domains in tandem.

In this complex material, the first scaffolding protein may include at least one first scaffolding protein having a cellulose-binding domain. In addition, the proteins may be selected from an enzyme group that degrades cellulose, and this enzyme may include two or more species selected from a group comprising at least β-glucosidase, endoglucanase and cellobiohydrolase. Preferably, all these enzymes may be selected. This complex material, as a result, is preferably provided with insoluble cellulose assimilation.

In the complex material of the present technique, the cell is preferably alcohol-producing yeast or organic acid-producing yeast. In addition, the cell may have no production capability of the proteins. In other words, the proteins may be a protein that is foreign to the cell.

According to the present technique, a method for preparing a protein complex material is provided with the step of supplying to an artificial scaffolding material that comprises a cell, scaffolding proteins and one species or two or more species of proteins. The scaffolding proteins are heterologous to the cell and placed contiguously to one another on the surface layer side of the cell, and provided with a plurality of non-covalently binding protein-binding domains arranged in tandem. Each of one species or two or more species of proteins has an interaction domain that can bind to the protein-binding domain from outside the cell, whereby the proteins are bound to the protein-binding domains of the artificial scaffolding material.

In this preparation method, one species or two or more species of proteins are preferably two or more species selected from an enzyme group that degrades cellulose. Furthermore, the cell is preferably yeast.

According to the present technique, a degradation method for degrading cellulose is provided with the step of bringing cellulose within a cellulose series material into contact with an enzyme complex material that comprises: a cell; scaffolding proteins that are heterologous to the cell, have a plurality of non-covalently binding protein-binding domains in tandem and are placed contiguously to one another on the surface layer side of the cell; and one species or two or more species of enzymes selected from an enzyme group that degrades cellulose bound to the protein-binding domain via a non-covalent bond, to degrade cellulose with the enzymes.

In addition, according to the present technique, a production method for producing a useful substance using cellulose is provided with the step of bringing cellulose within a cellulose series material into contact with an enzyme complex material that is provided with: a cell; scaffolding proteins that are heterologous to the cell, have a plurality of non-covalently binding protein-binding domains in tandem and are placed contiguously to one another on the surface layer side of the cell; and one species or two or more species of enzymes selected from an enzyme group that degrades cellulose bound to the protein-binding domain via a non-covalent bond, to degrade cellulose with the enzymes, and the step of assimilating the cellulose degradation product obtained by the enzymes with the cell of the complex material for conversion into a useful substance.

DETAILED DESCRIPTION OF THE PREFERRED EMBODIMENT

Figure 1:
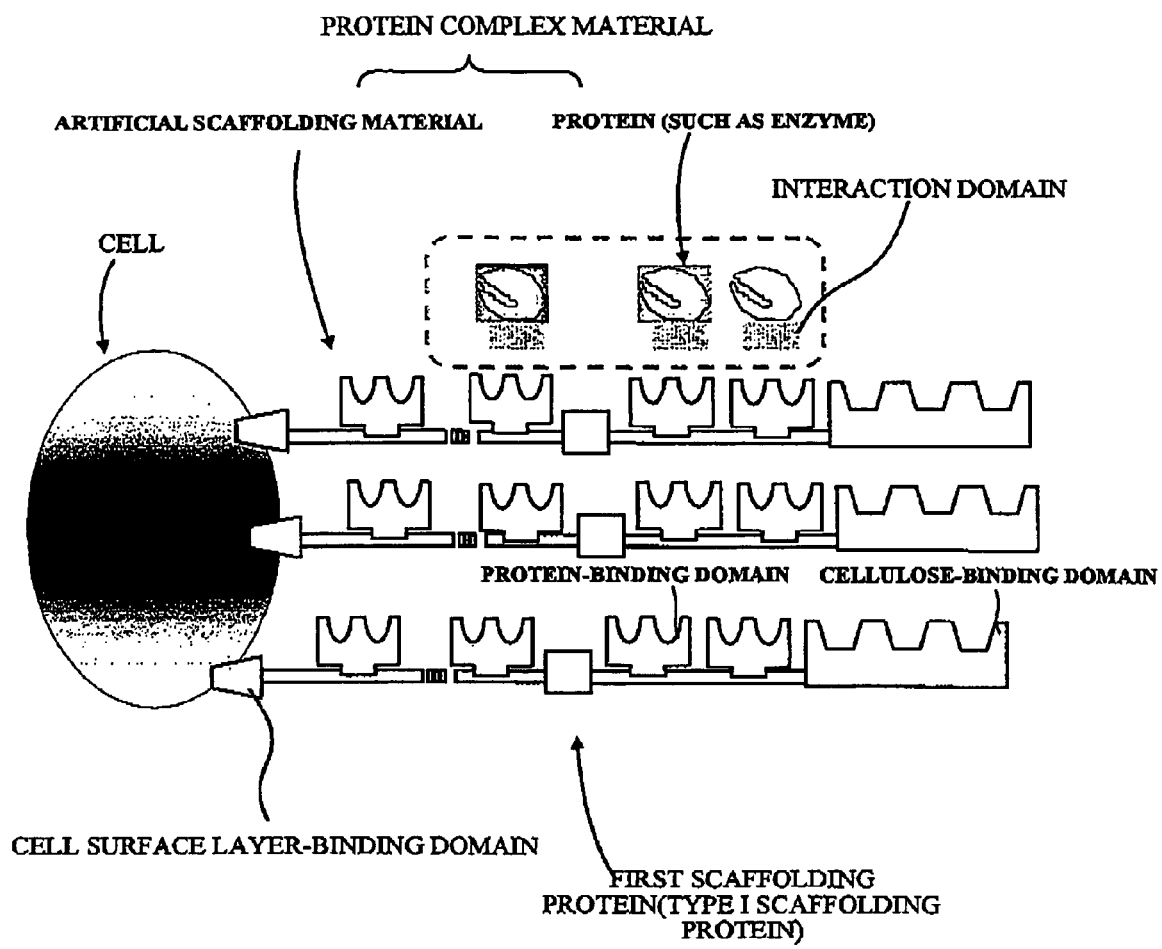
FIG. 1 shows one embodiment of the artificial scaffolding material of the present technique.

The present technique relates to artificial scaffolding material for retaining proteins and use thereof, the artificial scaffolding material of the present technique can be provided with a cell and scaffolding proteins, which are proteins that are heterologous to the cell and provided with a plurality of non-covalently binding protein-binding domains arranged in tandem and placed on the surface layer side of the cell at an extent that allows the cell to be conferred with aggregation properties. The state of the plurality of non-covalently binding protein-binding domains being arranged in tandem may also be defined as being aligned in series. Furthermore, the scaffolding proteins are positioned on the surface layer of the cell with the extent of density that may allow the cell to be conferred with aggregation properties. As shown in FIG. 1, when desired proteins are bound to protein-binding domains, these proteins can be arranged contiguously.

Figure 2:
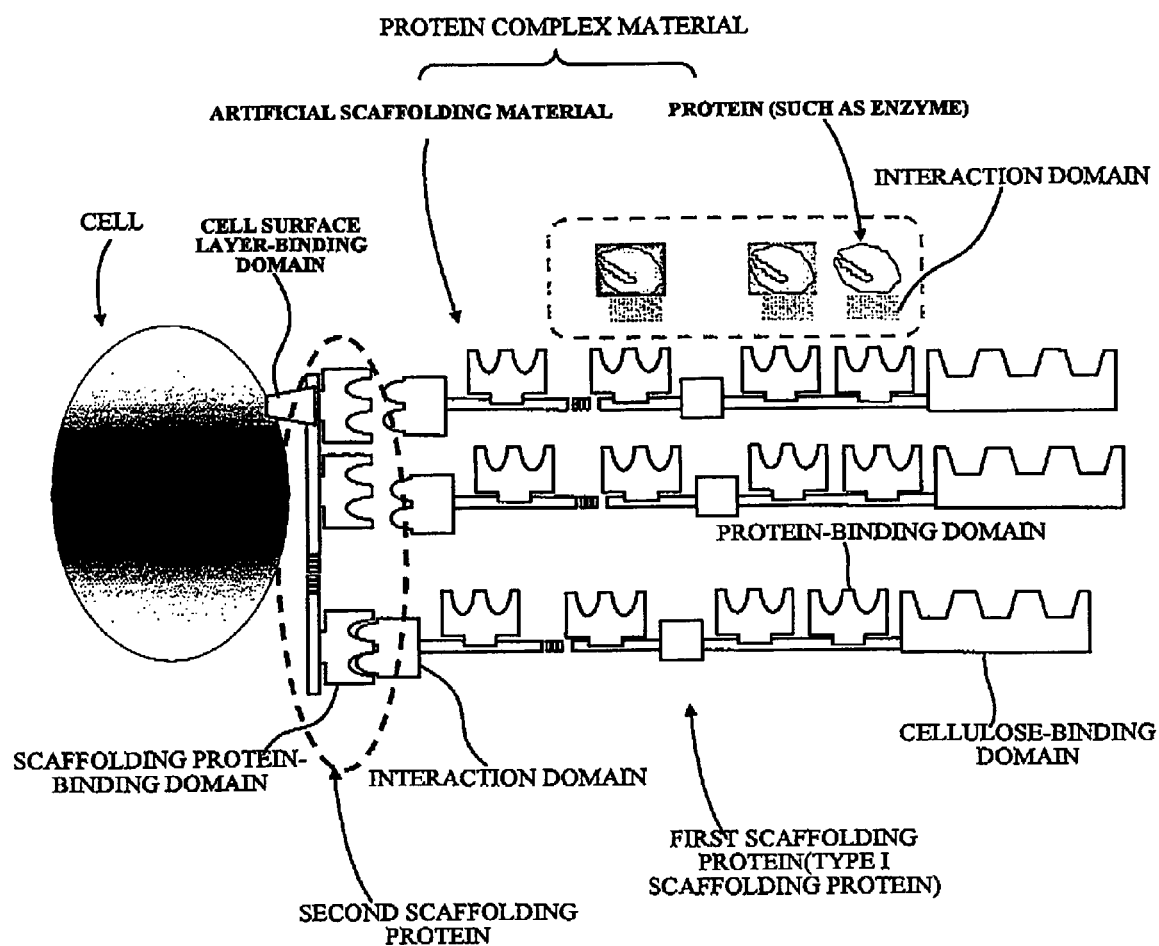
FIG. 2 shows another embodiment of the artificial scaffolding material of the present technique.

Specifically, the artificial scaffolding material of the present technique may be provided with a cell, first scaffolding proteins and a second scaffolding protein. The first scaffolding proteins are heterologous to the cell, and each of them has a plurality of non-covalently binding protein-binding domains arranged in tandem, and are placed on the surface layer side of the cell. The second scaffolding protein that is heterologous to the cell and has a plurality of scaffolding protein-binding domains that can each bind one of the first scaffolding proteins via non-covalent bond. The second scaffolding protein is placed on the surface layer of the cell. Each of the first scaffolding proteins has an interaction domain that binds one of the scaffolding protein-binding domains of the second scaffolding protein via a non-covalent bond. The interaction domain can be provided with a structure that enables the binding to the scaffolding protein-binding domain. Therefore, for instance, as shown in FIG. 2, the first scaffolding protein can be arranged according to the number of scaffolding protein-binding domains that the second scaffolding protein possesses, and as a result, a plurality of numbers and/or species of proteins can be arranged contiguously using the protein-binding domains of the first scaffolding protein.

With such artificial scaffolding material of the present technique, the protein-binding domains placed in tandem on the contiguously placed first scaffolding proteins can construct a two-dimensional protein-binding domain array. Using this domain array, a plurality of numbers and/or species of proteins can be placed contiguously and in an array form. Various proteins can be arranged two-dimensionally at will by using a protein-binding domain and the binding selectivity with respect to the domain.

The artificial scaffolding material of the present technique can be used in a protein complex material in which a plurality of numbers or a plurality of species of proteins such as enzymes have been complexed. The protein complex material of the present technique can be provided with one species or two or more species of proteins such as enzymes bound via a non-covalent bond to the protein-binding domains of such artificial scaffolding material. Since one species or two or more species of proteins are placed contiguously, such a protein complex material allows these proteins to function effectively. In particular, when multiple items or a plurality of species of enzymes are placed contiguously, an effective enzymatic reaction, such as allowing the reaction speed to greatly increase, may take place in enzymatic reaction systems where a plurality of species of enzymes work cooperatively or stepwise.

In relation to various embodiments of the present technique, artificial scaffolding material and preparation method therefore, protein complex material and preparation method therefore and substance production method using, protein complex material will hereinafter be orderly described.

(Artificial Scaffolding Material)

The artificial scaffolding material of the present technique can be provided with a cell and a plurality of scaffolding proteins (hereinafter referred to as first scaffolding proteins). The present artificial scaffolding material is a scaffolding material that allows one species or two or more species of proteins to be placed effectively and functionally, and is particularly suited to scaffolding material for retaining and causing a plurality of numbers and/or species of proteins to function.

(Protein)

In the present artificial scaffolding material, the protein intended to be retained therein is not limited in particular. In the employment of the present artificial scaffolding material, not only one species but two or more species of protein can be retained simultaneously. Preferably, they gather as a plurality of numbers and/or species of proteins that function cooperatively or stepwise. As such proteins, from the point of view of the structure thereof, having a peptide chain is sufficient. They may be protein complexes of a protein such as glycoprotein or lipoprotein, and other biological constituents or the like. In addition, from the point of view of the function thereof, proteins that function as, for instance, enzyme, antibody, receptor or antigen can be employed with the present artificial scaffolding material, with no particular limitation.

An enzyme is preferable as protein to be retained by the present artificial scaffolding material. In particular, the enzyme is preferably at least part of a group of the enzymes constituting an enzymatic reaction system in which a plurality of species of enzymes work cooperatively or stepwise. According to the present artificial scaffolding material, since a multiple items or a plurality of species of enzymes can be placed contiguously, overall reaction speed in an enzymatic reaction system requiring a plurality of enzymatic reactions can thereby be increased. As one example of such enzyme groups, cellulose, which defines the types of enzyme that degrades cellulose, and enzyme groups degrading starch can be employed. Regarding cellulase, detailed descriptions will be given later.

(Cell)

The present artificial scaffolding material can utilize a cell as a support for the first scaffolding proteins. As in the merits of using a cell as support are that: the first scaffolding proteins can be produced by the cell; the produced first scaffolding protein can be readily supported by an adequate method on the surface layer of the cell; such a cell can be grown; such cells can be further immobilized on another carrier; and while the useful substance are degraded and utilized, various reactions can be carried out effectively by selecting cells expressing the enzyme produced, or the like, and by carrying out such modification on the cell and the like.

For such cell, there are no particular limitations in the employment thereof. From the viewpoint of medical use, it may be a human cell or a nonhuman animal cell, and from the viewpoint of industrial use or the like, it may be a microorganism. As microorganisms, eukaryotic microorganisms, such as fungus and yeast, prokaryotic microorganisms, such as *Escherichia coli*, lactic acid bacterium and *Bacillus subtilis* can be employed. The microorganism to be used may be selected according to the protein intended to be retained in the present artificial scaffolding material, and in the application of the protein complex material described below, and the like. In addition, in relation to the protein intended to be retained, the microorganism may be a microorganism capable of autonomously producing the protein intended to be retained by the present artificial scaffolding material. Furthermore, the microorganism may not self produce such protein autonomously, that is to say, a microorganism that depends on the supply of such protein from the outside as a foreign protein. When using a microorganism that autonomously produces the protein intended to be retained by itself, there is the merit mat such protein need not be synthesized separately. On the other hand, when using a microorganism that does not produce the protein by itself, there is the merit that multiple quantities or multiple species of proteins can be provided without giving the burden of protein synthesis to the microorganisms.

As microorganisms, using yeast among the variety thereof is desirable. There is no particular limitation for the yeast. For instance, the yeast may be selected from the *Pichia* genus, the *Saccharomyces* genus and the *Candida* genus. As the *Pichia* genus, for instance, *Pichia pastoris* or the like can be employed. As the *Saccharomyces* genus, *Saccharomyces cerevisiae* or the like can be employed. In addition, as the *Candida* genus, *Candida krusei* or the like can be employed.

Note that, for the cell used in the present artificial scaffolding material, a suitable cell can be selected according to the application of the present artificial scaffolding material, and can be additionally modified and utilized. Regarding the selection of cell when the application is taken into consideration, detailed descriptions will be given later.

(First Scaffolding Protein)

The present artificial scaffolding material can be provided with first scaffolding proteins on the surface layer side of the cell. In other words, it is provided with first scaffolding proteins in an exposed state on the surface layer of the cell. The first scaffolding proteins can be provided to include one species or two or more species. If one species of first scaffolding proteins is to be used, proteins arranged on this scaffolding protein can be readily placed contiguously, and if two or more species of first scaffolding proteins are to be used, different species, combinations and numbers of proteins arranged on different scaffolding proteins can be readily placed contiguously. Note that the first scaffolding proteins can be distinguished by the types and the numbers of protein-binding domains thereof and combination thereof, as well as the presence or the absence of a cellulose-binding domain, or the like. In this sense, a variety in configuration may exist among the group of first scaffolding proteins.

The first scaffolding proteins are heterologous to the cell. That is to say, a first scaffolding protein can be a protein that the cell does not produce inherently. Preferably, the first scaffolding proteins are expressed by the cell as a result of the DNA coding for the first scaffolding proteins being introduced in an expressible manner into the cell. By having the first scaffolding proteins expressed as proteins heterologous with respect to the cell, a cell that does not express the first scaffolding proteins inherently also becomes usable as a support for the artificial scaffolding material. Various operations for the expression of heterologous proteins by such introduction of gene into various cells such as microorganisms may be learned from, for instance, Molecular Cloning A Laboratory Manual second edition (Maniatis et al., Cold Spring Harbor Laboratory press. 1989).

Each of the first scaffolding proteins is preferably a protein fundamentally constituted by a single stranded polypeptide chain. In addition, each of the first scaffolding protein preferably has a plurality of protein-binding domains that have the non-covalent binding characteristic and arranged in tandem. The state of "being in tandem" can be satisfied when a plurality of the domains are lined along a polypeptide chain, and regardless of the presence or absence of a spacing sequence between the lined protein binding domains, the fact that the spacing interval is constant and the presence of a heterogeneous domain. Preferably, a spacing sequence between domains is provided within the tandem.

A protein-binding domain is a domain that is capable of binding another protein having an interaction domain that is capable of binding to the protein-binding domain via a non-covalent bond, based on the amino acid sequence thereof. Since another protein can be bound via a non-covalent bond to the first scaffolding protein, such another protein can be readily bound to the first scaffolding protein or readily separated and recovered from the first scaffolding protein.

As such protein-binding domain and interaction domain, for instance, the relationship of an antigen with an antibody, the relationship of a ligand with a receptor, and the relationship of cohesin with dockerin in a cellulosome can be employed. In this case, protein-binding domains can be, respectively, an antigen or an epitope, a receptor and cohesin, while, as the interaction domain or protein possessing this proteins, antibody, ligand and dockerin or enzymes such as cellulase having dockerin, can be utilized.

By providing the protein of which the present artificial scaffolding material intends to bind and retain, with a suitable antibody or a portion thereof, a ligand or a portion thereof, or Type I dockerin against Type I cohesin, all of which function as interaction domain that binds via a non-covalent bond to the protein-binding domain of the first scaffolding protein, the first scaffolding protein can be enabled to bind and retain such protein.

As antigen or epitope applicable as a protein-binding domain in the first scaffolding protein of the present technique, the ZZ domain derived from Protein A of *Staphylococcus aureus*, or the like, can be utilized. In addition, as receptor usable as a protein-binding domain, the antibody Fc region, or the like, can be utilized.

Using the Type I cohesin domain in cellulosome as a protein-binding domain in the first scaffolding protein is desirable. The Type I cohesin domain is known as a domain that binds via a non-covalent bond cellulase having catalytic activity in Type I scaffolding protein (scaffolding protein) of cellulosome (cellulase complex) formed by various cellulosome-producing microorganisms shown in the following Table 1 (Sakka et al., Protein Nucleic Acid and Enzyme, Vol. 44, No. 10 (1999), p 41-p 50, Demain, A. L., et al., Microbiol Mol. Biol. Rev., 69 (1), 124-54 (2005), Doi, R. H., et al., J. Bacterol., 185 (20), 5907-5914 (2003), and the like). As such Type I cohesin domain, multiple sequences thereof have been determined in various cellulosome-producing microorganisms. The amino acid sequences and DNA sequences of these various Type I cohesins can be readily acquired from various protein databases and DNA sequence databases accessible through the NCBI home page (http://www.ncbi.nlm.nib-.gov/) or the like, and those skilled in the art can compose the first scaffolding protein having such Type I cohesin domain synthesized by gene recombination, or the like, as a heterologous protein inside a cell serving as a support for the present artificial scaffolding material. Note that such first scaffolding protein having Type I cohesin domain can also be obtained by chemical synthesis.

TABLE 1

| Cellulosome-producing microorganisms |
| --- |
| Anaerobic bacteria |
| *Acetivibrio cellulolyticus* <br> *Bacteroides cellulosolvens* <br> *Butyrivibrio fibrisolvens* <br> *Clostridium acetobutylicum* <br> *Clostridium cellulovorans* <br> *Clostridium cellobioparum* <br> *Clostridium cellulolyticum* <br> *Clostridium josui* <br> *Clostridium papyrosolvens* <br> *Clostridium thermocellum* <br> *Ruminococcus albus* <br> *Ruminococcus flavefaciens* <br> *Ruminococcus succinogenes* |
| Anaerobic fungi |
| *Neocallimastrix frontalis* <br> *Neocallimastrix particiarum* <br> *Orpnomyces* sp. <br> *Piromyces* sp. |

(Cellulosome)

A cellulosome is a cellulase complex formed by cellulolytic anaerobic microorganisms outside of the microbial body. Providing a cellulosome or a portion thereof as exogenous cellulase allows effective degradation of complex cellulose series material such as lignocellulose series material. In addition, cellulases can become to bind to cellulose more facilitately via a cellulosome.

A cellulosome is formed by anaerobic bacteria or anaerobic fungi outside the microbial body and in general exists bound to the surface of the microorganism or in the culture solution. As cellulosomes, be they cellulosomes produced by well known cellulosome-producing microorganisms such as anaerobic microorganisms including the microorganisms that form cellulosome shown in Table 1, cellulosomes to be unveiled in the future as well as variants thereof, any of such cellulosomes can be used for the first scaffolding protein of the present technique or the second scaffolding protein described below. Taking into consideration the level of cellulose degradation ability, cellulosome produced by a thermophilic anaerobic microorganism such as *Clostridium thermocellum* or bacteria of the *Clostridium* genus such as *Clostridium cellulolyticum* or a variant thereof, can be used in the present technique.

As at least one or a part of the protein-binding domain of the present artificial scaffolding material, for instance, Type I cohesin domains, such as, Type I scaffolding protein of *Clostridium thermocellum* and Type I scaffolding protein of *Clostridium josui* can be used. Preferably, Type I cohesin domains disclosed in *C. cellulolyticum* (NCBI home page http://www.ncbi.nlm.nih.gov/), Accession No.: U40345), *C. cellulovorans* (same home page, Accession No.: M73817), *C. acetobutylicum* (same home page, Accession No.: AE001437) can be utilized.

The first scaffolding protein has a plurality of such protein-binding domains arranged in tandem. There are no particular limitations on the configuration whereby the protein-binding domains are held. As has been described above, the first scaffolding proteins may have each domain connected directly, or may have the domains in a spaced state by a suitable linker. In addition, the plurality of protein-binding domains may be of an identical species of domain comprising one species of amino acid sequence, or may be domains comprising different amino acid sequences of two or more species. Using different species of protein-binding domains, different proteins can be arranged on the first scaffolding protein.

At least one of the first scaffolding proteins preferably possesses a cellulose-binding domain (CBD) of the Type I scaffolding protein of a cellulosome. The CBD is known to be a domain that binds cellulose, which is a substrate of cellulases (Sakka et. al, described above). The first scaffolding protein may have one or two or more cellulose-binding domains. Note that, the complex is not one that needs a cellulose-binding domain in the entirety of the first scaffolding proteins the cell is provided with. The first scaffolding protein having a cellulose-binding domain may be a portion of the entirety of the first scaffolding proteins with which the cell is provided.

Many amino acid sequences and DNA sequences of CBD in cellulosome of various cellulosome-producing microorganisms have been determined, and the amino acid sequences and the DNA sequences of these various CBDs can be readily acquired from various protein databases and DNA sequence databases accessible through the NCBI home page (http://www.ncbi.nlm.nih.gov/) or the like, and those skilled in the art can compose the first scaffolding protein having such CBD synthesized by gene recombination, or the like, as a heterologous protein inside a cell serving as a support for the present artificial scaffolding material. Note that such first scaffolding protein having CBD can also be obtained by chemical synthesis.

Regarding the protein-binding domain and CBD, the first scaffolding proteins can adopt the following morphologies. That is to say, the first scaffolding proteins may include (1) artificial proteins having Type I cohesins in tandem, (2) artificial proteins having Type I cohesins in tandem and further having CBD, (3) portions of Type I scaffolding protein derived from a cellulosome-producing microorganism where the Type I cohesins are connected in tandem, in its entirety or a portion thereof, and (4) portions of Type I scaffolding protein derived from a cellulosome-producing microorganism where cohesins are connected in tandem and simultaneously having at least one CBD, in its entirety or a portion thereof. Such first scaffolding proteins may be artificial proteins into which each element has been combined artificially. The first scaffolding proteins can also be variants) of Type I scaffolding protein of a cellulosome-producing microorganism. A variant means one that has been modified at least partially within the base sequence and/or amino acid sequence of the Type I scaffolding protein acquired cellulosome of cellulosome-producing microorganism. As such Type I scaffolding protein, the Type I scaffolding protein of *Clostridium thermocellum*, Type I scaffolding protein of *Clostridum josui*, or a variant thereof, may be used.

The first scaffolding proteins are preferably placed contiguously to one another in the surface layer of the cell. The reason is that this results in allowing other proteins binding within the first scaffolding proteins to be placed contiguously. From such a point of view, the first scaffolding proteins are preferably provided at an extent that allows the cell to be conferred with aggregation properties. Here, aggregation means the property of cells to aggregate or to aggregate and precipitate when cells are placed under ordinary liquid culture conditions, that is to say, when cells are suspended in an appropriate liquid culture medium. This is due to the fact that the aggregation properties of cells are assumed to be inherent to the interaction of protein-binding domains, and when aggregation properties are conferred to cells, these protein-binding domains are in a state where they are contiguous to one another or in a state where they can become contiguous.

In addition, it is also desirable on the points that the acquisition of aggregation properties by cells allows, when causing the artificial scaffolding material to retain proteins such as enzymes for industrial use as in an enzyme complex material, and when this enzyme complex material is aggregated, enzymes can be placed contiguously, and in addition, effective recovering and repeated use of the enzyme complex material can be facilitated.

When conferring aggregation properties to cells with the first scaffolding proteins, at least one of the first scaffolding proteins preferably has three or more protein-binding domains. This is because if there are three or more of protein-binding domains existing, when the first scaffolding proteins are placed contiguously, conferring aggregation property of the cell tends to become facilitated in a greater degree. Preferably, four or more of protein-binding domains should be provided. This is because if there are four or more protein-binding domains, conferring aggregation property of the cell becomes clearly facilitated. From the point of view of aggregation property, there are no particular limitations on the upper limit in the number of protein-binding domains. Note that from the point of view of facilitating maintaining expression quantity, there are cases where on the order of seven or less is desirable. Furthermore, it should be noted that, in the term of 'at least one of the first scaffolding proteins having three or more protein-binding domains', cases such as some or a plurality of the first scaffolding proteins having three or more protein-binding domains may be included. Further, the aforementioned term may include a case in which a part of the first scaffolding proteins comprise three or more protein-binding domains, while the rest of the first scaffolding proteins comprise two or less. Moreover, there also may be a case where all of the first scaffolding proteins having three or more protein-binding domains. The number of domains comprised by the respective first scaffolding protein may vary among the first scaffolding proteins. The same condition can be defined of first scaffolding proteins having four or more domains and/or seven or less domains.

Such first proteins are disposed on the surface layer side of cells. One mode whereby the first scaffolding protein is provided on the surface layer side of cell may be a mode whereby the first scaffolding protein is bound to the surface layer of cell directly via a non-covalent bond or a covalent bond. For binding onto the cell surface layer, a well-known cell surface layer display system of protein can be used. For instance, when using yeast as the cell, the surface layer protein α-agglutinin or the receptor thereof can be used. A cell surface layer display system for protein using agglutinin can be obtained, for instance, as a display kit for yeast from Invitrogen containing pYD1 vector and EBY100 *Saccharomyces cerevisiae*. In addition, systems using cell surface layer proteins such as SAG1, and FLO1 to FLO11, or the like, can be used as cell surface layer display system. Regarding such binding morphologies, in order to bind directly to the cell surface layer, the first scaffolding protein can have a cell surface layer binding domain required in these various systems.

(Second Scaffolding Protein)

Another mode whereby the first scaffolding proteins are provided to the surface layer of a cell may be a mode whereby the first scaffolding proteins are retained on the surface layer side of the cell as a result of being bound via non-covalent bonds to a second scaffolding protein bound to the surface layer of the cell. The second scaffolding protein is a protein that is heterologous to the cell, has a scaffolding protein-binding domain that can bind the first scaffolding protein via a non-covalent bond and is placed on the surface layer side of the cell.

The second scaffolding protein is a protein fundamentally constituted by a single stranded polypeptide chain and has a plurality of scaffolding protein-binding domains that can bind the first scaffolding proteins via non-covalent bonds. In the present technique, a scaffolding protein-binding domain is a domain that is capable of binding a first scaffolding protein having an interaction domain that binds via a non-covalent bond the scaffolding protein-binding domain, based on the amino acid sequence thereof. Since the first scaffolding proteins can each be bound via a non-covalent bond to the second scaffolding protein, the first scaffolding proteins can be bound readily against the second scaffolding protein or readily separated and recovered from the second scaffolding protein.

As such scaffolding protein-binding domains and interaction domains, similarly to the protein-binding domains in the first scaffolding protein already described, relationship of an antibody to an antigen or an epitope, the relationship of a ligand and receptor and the relationship of cohesin an dockerin in a cellulosome can be given as examples. In these relationships, as of the scaffolding protein-binding domains, there can be respectively antigen or epitope, receptor and cohesin, while, the interaction domain or protein possessing this, antibody, ligand and dockerin or Type I scaffolding protein having dockerin, and the like, can be cited.

As scaffolding protein-binding domain, similarly to the protein domain in the first scaffolding protein, various antigens, epitopes, various receptors and cohesins can be used, and preferably, using the Type II cohesin domain of Type II scaffolding protein (also called anchor protein) constituting the cellulosome of a cellulosome-producing microorganism is desirable.

The Type II cohesin domain is known to be a domain for retaining Type I scaffolding protein on Type II scaffolding protein via a non-covalent bond in a cellulosome (Sakka et al, Protein, Nucleic Acid and Enzyme, Vol. 44, No. 10 (1999), p 41-p 50, or the like). It is known that the Type II dockerin domain that the Type I scaffolding protein possesses binds to the Type II cohesin domain of the Type II scaffolding protein. As such Type II cohesin domain, multiple sequences thereof have been determined in various cellulosome-producing microorganisms. The amino acid sequences and DNA sequences of these various Type II cohesins can be readily acquired from various protein databases and DNA sequence databases accessible through the NCBI home page (http://www.ncbi.nlm.nih.gov/) or the like, and those skilled in the art can have such second scaffolding protein having Type II cohesin domain synthesized by gene recombination, or the like, as a heterologous protein inside a cell serving as a support for the present artificial scaffolding material. Note that such second scaffolding protein having Type II cohesin domain can also be obtained by chemical synthesis.

When placing the first scaffolding proteins on the cell surface layer side with the second scaffolding protein in between, each of the first scaffolding proteins is preferably provided with a suitable antibody or a portion thereof, a ligand or a portion thereof, or a Type II dockerin domain against Type II cohesin, which functions as an interaction domain that binds via a non-covalent bond to a scaffolding protein-binding domain in the second scaffolding protein. Note that the Type II dockerin domain is known to be a domain for retaining Type I scaffolding protein on Type II scaffolding protein via a non-covalent bond in a cellulosome (Sakka et al, Protein, Nucleic Acid and Enzyme, Vol. 44, No. 10 (1999), p 41-p 50, or the like). As such Type II dockerin domain, multiple sequences thereof have been determined in various cellulosome-producing microorganisms. The amino acid sequences and DNA sequences of these various Type II dockerin domain can be readily acquired from various protein databases and DNA sequence databases accessible through the NCBI home page (http://www.ncbi-nlm.nih.gov/) or the like, and those skilled in the art can compose such first scaffolding protein having Type II dockerin domain synthesized by gene recombination, or the like, as a heterologous protein inside a cell serving as a support for the present artificial scaffolding material. Note that such first scaffolding protein having Type II dockerin domain can also be obtained by chemical synthesis.

As the scaffolding protein-binding domains in the second scaffolding protein, for instance, Type II cohesin domains of Type II scaffolding proteins such as Type II scaffolding proteins of *Clostridium thermocellum*, and Type II scaffolding proteins of *Clostridum josui* can be used. Among them, the Type II cohesin domains disclosed in ScaB sequence of *A. Cellulolyticus* (NCBI home page, Accession No.: AY221112) can be employed.

Although the second scaffolding protein may have only one such scaffolding protein-binding domain, it is preferably provided with the plurality in tandem. Having a plurality allows the first scaffolding proteins to be arranged along the second scaffolding protein, while at the same time, allowing readily the first scaffolding proteins and the desired proteins bound to the first scaffolding proteins to be placed contiguously. In addition, larger number of first scaffolding proteins can be bound on the surface layer side of cell than in a case where first scaffolding proteins are directly bound on the surface layer of cell. Resulting from these, an artificial scaffolding material can be provided, capable of binding and retaining a desired protein at a high density in the cell surface layer. Note that since the second scaffolding protein binds the first scaffolding proteins via non-covalent bonds, an artificial scaffolding material that is capable of binding and retaining readily more of the desired proteins more contiguously can be provided.

Note that there are no particular limitations on the mode whereby the scaffolding protein-binding domains are held in the second scaffolding protein. As has been described above regarding the protein-binding domains, the second scaffolding protein may have each domain connected directly, or may have the domains in a spaced state by a suitable linker therebetween.

In addition, the plurality of protein-binding domains may be of an identical species of domain comprising one species of amino acid sequence, or may be domains comprising different amino acid sequences of two or more species. Using different species of scaffolding protein-binding domains, different first scaffolding proteins can be arranged on the second scaffolding protein.

The second scaffolding protein must be bound on the surface layer side of a cell. The second scaffolding protein is bound to surface layer of a cell via a covalent bond or a non-covalent bond. When the second scaffolding protein is bound to the surface layer of cell via a covalent bond, there is a merit that the second binding protein is not separated from the cell and is retained even by washing or the like, and if it is bound via a non-covalent bond, in contrast, there is a merit that the second scaffolding protein and first scaffolding proteins can be separated from the cell by washing or the like. In either case, the second scaffolding protein has a binding domain for binding to the cell surface layer.

Various cell surface layer display systems as aforementioned can be used as systems for binding the second scaffolding protein on the surface layer side of a cell. In order to bind it directly to the cell surface layer, second scaffolding protein can have a cell surface layer binding domain required in these various systems.

As such a second scaffolding protein, alternatively to a fusion protein into which each element described above has been combined artificially, it may also be a variant of a Type II scaffolding protein of a cellulosome-producing microorganism. A variant means one that has been modified at least partially within the base sequence and/or amino acid sequence of the Type II scaffolding protein obtained from cellulosome of cellulosome-producing microorganism. As such Type II scaffolding protein, Type II scaffolding protein of *Clostridium thermocellum*, Type I scaffolding protein of *Clostridum josui*, or a variant thereof can be used.

The present artificial scaffolding material can be characterized by the types and numbers of protein-binding domains and combinations thereof in the first scaffolding proteins, as well as the morphology of the second scaffolding protein, and the like. In such characterization, the present artificial scaffolding material can use identical artificial scaffolding material or can use different artificial scaffolding materials in combination.

As described above, the artificial scaffolding material of the present technique can place first scaffolding materials which in each having a plurality of protein-binding domains contiguously on the cell surface layer side. Therefore, an artificial scaffolding material that is desirable for retaining proteins contiguously may thereby be configured. In particular, an artificial scaffolding material capable of retaining contiguously multiple items or a plurality of species of proteins such as enzymes may be configured. In addition, an artificial scaffolding material that is capable of retaining proteins in the form of a two-dimensional array may be configured.

In addition, in a case where the artificial scaffolding material is provided with aggregation properties, when used as a protein complex material that has retained proteins such as enzymes, the proteins can be placed all the more in a contiguous manner, in addition to being appropriate for repeated use.
(Method for Preparing Artificial Scaffolding Material)

In such artificial scaffolding material, for instance, when binding the first scaffolding proteins directly onto the cell surface layer, it suffices to cause the cell to autonomously produce the first scaffolding proteins in which each having a cell surface layer binding domain and to secrete the self-produced proteins (the first scaffolding proteins) to outside of the cell in a state that allows binding to the cell surface layer. The first scaffolding proteins are respectively heterologous to the cell. In general, it suffices to introduce in an expressible manner into a cell a DNA coding for such heterologous protein using a gene recombination method, and as consequence have the first scaffolding protein be expressed in the cell.

In addition, when binding the first scaffolding proteins via the second scaffolding protein to the cell surface layer, it suffices that the first scaffolding proteins and the second scaffolding protein are respectively expressed in cells through genetic recombination or the like and be secreted to outside the cells, while at the same time, an assembly is constructed on the surface layer of cell, in which respective first scaffolding proteins are bound to the second scaffolding protein that is bound by the cell surface layer. In this case, the second scaffolding protein is preferably provided with a cell surface layer binding domain based on a cell surface layer display system, and each of the first scaffolding proteins is preferably provided with an interaction domain (antibody, ligand and Type II dockerin, or the like) that binds to the respective scaffolding protein-binding domain of the second scaffolding protein via a non-covalent bond.

The first scaffolding proteins and the second scaffolding protein, using non-covalent bonding by the combination of Type D cohesin and Type II dockerin in a cellulosome, allows an artificial scaffold comprising the first scaffolding protein and the second scaffolding protein to be constructed readily on the surface layer of the cell. In addition, if a cell surface layer display system such as agglutinin described above, or the like, is utilized, the second scaffolding protein can also be provided from outside the cell.

Note that the artificial scaffolding material can also be prepared by expressing in a cell the second scaffolding protein only to prepare a cell in which the second scaffolding material has been placed on the surface layer side of the cell, and providing from outside the first scaffolding proteins with respect to the cell, and constructing an artificial scaffold provided with the first scaffolding proteins and the second scaffolding protein. According to such preparation method, since the first scaffolding proteins need not be synthesized by the cell; it is suitable when placement of a large amount or multiple species of the first scaffolding proteins on the cell surface layer is intended. The artificial scaffolding material provided on the surface layer side of cell with only the second scaffolding protein used in this preparation method is also included in one embodiment of the present technique.

According to the method for preparing the artificial scaffolding material of the present technique, an artificial scaffold readily allowing proteins to be placed contiguously can be constructed on the cell surface layer. By having the first scaffolding proteins and the second scaffolding protein synthesized inside the cell and secreted outside the cell and using a cell surface layer display system or bond with non-covalent traits between the respective first scaffolding protein and the second scaffolding protein, an artificial scaffolding material having a protein domain that can retain proteins contiguously may be obtained without using any complex methods. As a method modified from the method for preparing the artificial scaffolding material of the present technique, even if only the second scaffolding protein is bound and placed on the cell surface layer and the first scaffolding proteins are provided from outside such cell, the first scaffolding proteins and the second scaffolding protein are bound by non-covalent bonds, such that an artificial scaffold comprising these scaffolding proteins on the cell surface layer can be formed.
(Protein Complex Material)

The protein complex material of the present technique can be provided with a cell, first scaffolding proteins and one species or two or more species of proteins. The first scaffolding proteins are heterologous to the cell, and provided with a plurality of protein-binding domains that is capable of non-covalently binding the one species or two or more species of proteins. Further, the first scaffolding proteins are arranged in tandem and placed contiguously to one another on the surface layer side of the cell. Each of the one species or two or more species of proteins is bound to the respective protein-binding domain via a non-covalent bond. This can also be termed as, in a case there are a plurality of one species or two or more species of proteins and protein-binding domains, there will exist a plurality of non-covalent bonds that binds each of the aforesaid proteins to respective protein-binding domain. In this case, the number of non-covalent bonds corresponds to the number of pairs formed of the aforesaid protein and protein-binding domain.

The cell and the first scaffolding proteins in the present complex material correspond to the cell and first scaffolding proteins in the artificial scaffolding material, and the various embodiments thereof that have been described above as in the artificial scaffolding material may be applied to the present complex material. In addition, morphology in which the present artificial scaffolding material is provided with a second scaffolding protein may also be applied to the present complex material.

The present complex material can bind and retain a desired protein via a non-covalent bond in the protein-binding domain of the first scaffolding protein. As such protein, proteins having various structures and functions, which have been already described above, may be employed. The protein that is bound and retained has an interaction domain that binds non-covalently to the corresponding protein-binding domain. The protein that is bound and retained can adopt the morphology of a fusion protein in which such interaction domain has been artificially fused, or of a protein inherently having such interaction domain. The amino acid sequence of such interaction domain is determined by the relationship with the protein-binding domain of the first scaffolding protein. That is to say, it is determined by the type of protein-binding domain (antigen, epitope, receptor and Type I cohesin) and furthermore, the selectivity of each type to individual protein-binding domain. Such protein having an interaction domain can be acquired readily for those skilled in the art by genetic engineering methods and others.

The present complex material is suited for binding and retaining a plurality of species of proteins. There are no particular limitations on the mode whereby the plurality of species of proteins are retained. For instance, two or more species of proteins may be bound and retained on one species of first scaffolding proteins, different proteins with respect to two or more species of first scaffolding proteins may respectively be bound and retained, and these retention morphologies may be combined. The mode whereby a plurality of species of proteins are bound and retained can be designed variously according to the combination of the protein-binding domain in the first scaffolding protein and the interacting domain.

(Complex Material Binding and Retaining an Enzyme)

The present complex material preferably has bound and is retaining enzyme as protein. This is because the merit such as in the speed factor of enzymatic reaction is significant, when multiple items or a plurality of species of enzymes are placed contiguously. In particular, it is desirable to bind and retain a portion or the entirety of the enzymes constituting an enzymatic reaction system in which a plurality of species of enzymes works cooperatively or stepwise. This is because, in such an enzymatic reaction system, placing contiguously related enzymes can accelerate the overall reaction speed.

As enzymes constituting such an enzymatic reaction system, they can be configured of a plurality of species of enzymes constituting a reaction system in which a plurality of types of reactions selected from various synthesis reactions, conversion reactions, transfer reactions, degradation reactions and the like, have been combined (for instance, a plurality of species of syntheses reaction may have been combined). As a reaction system in which a plurality of degradation reactions has been combined, reaction systems that degrade various artificial macromolecular materials and natural macromolecular materials can be employed. Among them, reaction systems allowing degradation of biopolymer materials can be employed. As such biopolymer materials, protein, lignin and polysaccharides such as starch, cellulose and the like, can be utilized. The present complex material can be used as a complex material for degrading these various macromolecular materials (enzymatic materials).

(Complex Material for Degrading Cellulose)

In a case where the present complex material binds and retains cellulase, the present complex material can be used as a complex material for degradation of cellulose. Cellulose is effectively degraded only when a plurality of enzymes work cooperatively and stepwise. In particular, this tendency exists in insoluble cellulose and crystalline cellulose. Since the present complex material can be provided with a plurality of species of cellulases arranged contiguously, it can degrade cellulose effectively. In particular, it can be optimized for degradation of cellulose by using Type I cohesin or a Type I scaffolding protein containing the same as the protein-binding domain of the first scaffolding protein. Further, in addition to these, using Type II cohesin or a Type II scaffolding protein containing the same as the second scaffolding protein. In addition, when a CBD is provided in some of the first scaffolding proteins and the cell can adsorb to the cellulose, or the like, cellulose can be degraded all the more effectively.

The cellulolytic enzymes (cellulases) used to cause the present complex material as a cellulose degrading material suffice to be those selected from the enzyme group comprising enzymes that are active in the process whereby cellulose in which D-glucoses are bonded by β-1,4 bonds is hydrolyzed and degraded into D-glucoses, and the origin thereof is also not limited in particular. Therefore, as cellulases, for instance, cellulolytic enzymes that have been given the number EC3.2.1.X in the International Union of Biochemistry and Molecular Biology can be cited. As enzymes that have been given this number, endoglucanase (1,4-β-D-glucan gluycanohydrase, EC3.2.1.4), β-glucosidase (EC3.2.1.21), 1,4-β-glucosidase (EC32.1.74) and exocellobiohydrolase (cellulose 1,4-β-cellobiosidase, EC3.2.1.91) can be cited. The cellulase used in the present technique may be only one species selected from such cellulases, or two or more species may be combined. Note that, cellulase may include enzymes contributing to the above degradation process, in activities that give rise to different effects from those described above.

The present complex material is preferably provided with two or more species of cellulase. More preferably, it contains one species or two species selected from endoglucanase and exocellobiohydrolase. The provision of these enzymes allows crystalline or insoluble cellulose to be degraded. The provision of these enzymes allows crystalline or insoluble cellulose to be degraded all the more efficiently. This is because these cellulases are assumed to act synergistically on cellulose and allow efficient degradation. In addition, it is desirable that either or both of β-glucosidase and 1,4-β-glucosidase is provided, which act on new low molecular cellulose and cellobiose, which are products of cellulose decomposition by these cellulases. All the more preferably, β-glucosidase, endoglucanase and exocellobiohydrolase may be provided.

While there are no particular limitations on the origin of the cellulase, cellulases constituting the cellulosome of cellulosome-producing microorganisms such as those shown in Table 1, cellulases produced by cellulolytic microorganisms shown in the following Table 2, and variants thereof, can be used for the cellulase. A variant means, one that has been modified at least partially within the base sequence and/or amino acid sequence of a naturally cellulase or a cellulase acquired from a cellulosome. Note that the modification includes, in addition to any or two or more of an insertion, a substitution, a deletion and an addition of an amino acid, modifications that do not influence the amino acid sequence.

The cellulase can be acquired from various natural cellulase-producing microorganisms shown in the following table or microorganisms artificially modified to form cellulase or a variant thereof or a portion thereof. Such modified microorganisms may be those having as parental strain or host the microorganisms derived from the following table, or may be those having as parental strain or host a microorganism suitable for industrial use, such as yeast. It is normal for cellulases to be secreted outside the microbial body of the microorganism, and cellulases can be readily acquired by recovering the cellulase-active fraction from the culture solution of these microorganisms. In addition, they can also be acquired via a cell-free protein synthesis system.

TABLE 2

| Non-cellulosome-producing microorganisms |
|---|
| Aerobic bacteria |
| *Celluomonas fimi*<br>*Thrmomonaspra fusca*<br>Anaerobic bacteria |
| *Cardicellulosiruptor saccharolyticum*<br>*Fibrobacter succinogenes*<br>Aerobic fungi |
| *Trichoderma reesei*<br>*Trichoderma viride*<br>*Aspersillus acculeatus*<br>*Aspergillus nigar*<br>*Acremonium cellulolyticus* |

TABLE 2-continued

Non-cellulosome-producing microorganisms

Basidiomycete

*Phanerochaete chrysosporium*

When the present complex material binds and retains cellulase, it may also bind and retain enzymes other than cellulase. For instance, being provided with an enzyme that degrades hemicellulose inside a lignocellulose series material, such as xylanase and hemicellulase, the complex material becomes capable of degrading hemicellulose inside the lignocellulose series material. For instance, activities such as xylanase, lichenase and mannanase have also been found in the cellulosome of *Clostridium thermosellum*. In addition, lignin peroxidase and manganese peroxidase, which degrade lignin, may be provided. If a lignin-degrading enzyme is provided, the present complex material can be used not only for degradation of a cellulose series material, but also for degradation of lignocellulose series material. Note that lignocellulose series material can be degraded by the combined use of a complex material that binds and retains a lignin-degrading enzyme to degrade lignin, or the lignocellulose series material can also be degraded by the use of the aforesaid isolated lignin-degrading enzyme separately.

In addition, when the present complex material binds and retains cellulase, cell in the present complex material is preferably a cell having capability of assimilating cellobiose, which is a product of decomposition of cellulose, or glucose, which is the final decomposition product, and also having a high capacity to assimilate either of these decomposed products. When using such a cell, at the surface layer of the cell, these decomposition products can be taken into the cell and used effectively.

The cell is preferably a microorganism capable of converting glucose into useful resources, such as, alcohol such as ethanol and organic acid such as lactic acid. When such a microorganism is used as a cell for the artificial scaffolding material, the present complex material can degrade cellulose and effectively assimilate the obtained decomposition product for direct conversion into a useful substance. That is to say, it can be used not merely as a degradation material that degrades a cellulose series material, but as a cellulose-assimilation material that can assimilate a cellulose series material for conversion into a useful substance. In a case where the microorganism is an ethanol-producing microorganism that has ethanol production capability, it can be used as a cellulose-assimilating ethanol conversion material that can produce ethanol, which is one kind of a useful substance, from cellulose, which is a non-edible sugar, at the same time as it can also provide carbon neutral fuel. In addition, when the microorganism is an organic acid-producing microorganism, such as of lactic acid, having lactic acid production capability, the present complex material can be used as a cellulose-assimilating lactic acid conversion material that can assimilate a cellulose series material for conversion into an organic acid such as lactic acid.

As ethanol-producing microorganisms, microorganisms that produce ethanol inherently such as yeast are adequate, and ethanol-producing microorganisms that have been artificially gene modified by gene recombination, or the like, are also adequate. As such ethanol-producing microorganisms, various yeasts from the *Saccharomyces* genus such as *Saccharomyces cerevisiae* and *Pichia* genus yeast such as *Pichia pastoris* can be utilized. In addition, yeast with resistance, against acid and salt reinforced by gene recombination can be utilized. As one example of such yeast, the MF-121 strain described in Japanese Patent Application Publication No. 2004-344084 can be cited. Note that all of the contents of this publication are hereby incorporated by reference into the present application.

As organic acid-producing microorganism, a well-known transformant rendered capable of producing organic acid such as lactic acid by gene modification taking as host a microorganism such as yeast can be used. Transformed yeast as such the lactic acid-producing yeast is disclosed in, for instance, Japanese Patent Application Publication No. 2003-334092, Japanese Patent Application Publication No. 2004-187643, Japanese Patent Application Publication No. 2005-137306, Japanese Patent Application Publication No. 2006-6271, Japanese Patent Application Publication No. 2006-20602, Japanese Patent Application Publication No. 2006-42719, Japanese Patent Application Publication No. 2006-75133, Japanese Patent Application Publication No. 2006-296377 and the like, and these transformed yeasts can be used in the present technique. Note that all of the contents of the publications are hereby incorporated by reference into the present application.

Note that, the present complex material for cellulose degradation can be used widely as enzymatic material for degrading cellulose within a cellulose series material. Here, "cellulose series material" means a material containing cellulose, which is a β-glucan comprising D-glucoses glycosidically linked via β-1,4 bonds. As "cellulose series material", containing cellulose is sufficient, and any origin or morphology may be adequate. Therefore, as cellulose series materials, various cellulose series materials, such as, for instance, lignocellulose series material, crystalline cellulose material, insoluble cellulose material and the like may be included. As lignocellulose series materials, for instance, lignocellulose series materials in a complexed state with lignin, or the like, in the woody portion and the leave portion of woody plants and leaf, stem, root and the like, of herbaceous plants can be utilized. As such lignocellulose series materials, they may be wastes such as, for instance, agricultural wastes, for example rice straws, wheat straws, stems and leaves of corns, and bagasses, collected woods, branches, dead leaves and the like or chips obtained by fibrillating these, scrap woods from saw mills such as sawdusts and chips, forest land remains such as thinned woods and damaged trees, and construction scrap woods. As crystalline cellulose series materials and insoluble cellulose series materials, crystalline or insoluble cellulose series materials containing crystalline cellulose and insoluble cellulose after separation of lignin or the like from a lignocellulose series material can be cited. As cellulose materials, in addition, used fiber products, such as, used paper containers, old papers and used clothes, and pulp waste liquors may be the origin. In addition, cellulose produced by cellulose-producing microorganisms, such as, *Acetobacter xylinum*, may be the origin.

Note that, when the present complex material can degrade and assimilate a cellulose series material, the present complex material per se can be multiplied with cellulose without using an edible sugar such as glucose. According to the present complex material, the quantity of edible sugar used, such as glucose, can be decreased by an important amount, or the use or edible sugar can be avoided.

In addition, prior to degradation by the present complex material, the cellulose series material may undergo a suitable pretreatment to facilitate degradation by cellulase. For instance, it may be uncrystallized cellulose. Uncrystallization of cellulose is often accompanied by simultaneous molecular decrease or weight decrease.

For instance, by partially hydrolyzing cellulose under acidic conditions with an inorganic acid such as sulfuric acid, hydrochloric acid, phosphoric acid or nitric acid, cellulose can become uncrystallized or lower molecular or weight. In addition to this, uncrystallization or low molecular transformation of cellulose can also be carried out by treatments such as supercritical water treatment, alkali and pressurized hot water treatment, or the like.

Note that the decomposition products obtained by the present complex material for degrading cellulose differ depending on the cellulose series material to be degraded, the type of cellulase that binds and retains, and the like. Therefore, they may not necessarily be ones with D-glucose as the end product, but may have a decomposition product composition having cellobiose and/or oligosaccharides as the main body.

In addition, by suitably selecting the enzyme that binds and retains, the present complex material can be used as an enzymatic material that degrades a macromolecular material other than the above cellulose (for instance, starch degradation material or the like), and can also be used as an enzymatic material for other reaction systems.

Note that the present complex material can be provided with a second scaffolding protein, and preferably, a second scaffolding protein having a plurality of scaffolding protein-binding domains. Provision of such a second scaffolding protein, a large number of first scaffolding proteins can readily be contiguous and placed on surface layer side of cell. As a result, protein of the enzyme bound to the protein-binding domain on the first scaffolding proteins can be retained contiguously. In addition, if there is a plurality of scaffolding protein-binding domains provided, the desired proteins can be more contiguous and bound and retained on the surface layer side of cell in a greater number. Such present complex material allows the reaction speed of a cooperative or stepwise reaction system by a plurality of species of proteins to be accelerated.

If the second scaffolding protein is bound to the surface layer of cell via a covalent bond, since the second scaffolding protein is fixed with respect to the cell, the artificial scaffolding material can be readily preserved, which is advantageous for handling or the like.

As described above, since the present complex material allows desired proteins to be placed contiguously, the function thereof can be expressed more effectively. In particular, reaction speed of a reaction system involving a plurality of species of enzymes can be accelerated. Therefore, it can be used as a material for degrading difficult-to-degrade materials such as biopolymer materials.

In addition, if the cell is provided with a function that further takes up into the cell and assimilates a product generated by the one or more protein retained and bound on one or more of first scaffolding protein (decomposition product) for conversion into a useful substance, a reaction system on the surface layer side of cell and a reaction system inside the cell can be constructed. As a result, a complex material can be obtained for carrying out degradation of macromolecular material outside the cell, acquiring and introducing into the cell the substrate for assimilation or the like, and carrying out assimilation and conversion inside the cell. According to this complex material, since it is provided with enzymes for degradation at a high density in the vicinity of the cell surface layer, substrates can be acquired at high concentrations in the vicinity of the cell surface layer, in addition, can be effectively introduced into the cell, effectively assimilated, converted and the like.

The present complex material can be retained on other supports. In general, it can be retained on a suitable solid phase carrier through a cell. By adopting such a morphology, repeated use can be realized economically in a step of culture or fermentation. As solid phase carriers where cells are retained, they can be porous particles, or compacts, fiber and the like of organic material or inorganic material. In addition, for methods for retaining a microorganism onto these carriers, it suffices to adopt prior art well-known methods.

(Method for Preparing the Present Complex Material)

The method for preparing the present complex material comprises the step of supplying an artificial scaffolding material with one species or two or more species of proteins having an interaction domain that is capable of binding to the protein-binding domain on the first scaffolding protein through secretion from inside the cell or supplied from outside the cell, and allows the present complex material to be obtained by binding each of the one species or two or more species of proteins to the respective protein-binding domain. According to the present preparation method, by supplying a desired protein that is intended to be bound and retained, from inside the cell or from outside the cell to the artificial scaffolding material, which is provided with an artificial scaffold for binding and retaining a protein on the cell surface, the desired protein can be readily retained contiguously on the surface layer of the cell. In addition, according to this method, a protein complex material can be readily provided, which is capable of increasing the reaction speed of a reaction system in which a plurality of species of enzymes works cooperatively or stepwise.

The desired protein provided to the artificial scaffolding material may be synthesized inside the cell by gene recombination, as necessary. Note that, when synthesizing inside the cell a protein intended to be bound and retained, it is synthesized as a fusion protein provided with a suitable secretion signal or interaction domain, as needed. The protein intended to be bound and retained is preferably supplied from outside the cell. If the desired protein has a suitable interaction domain, the protein-binding domain of the first scaffolding protein can be caused to bind and retain it even if it is supplied from outside the cell to the present artificial scaffolding material. In addition, supplying from outside the cell allows an as much as desired amount of protein that is intended to be bound and retained to be bound and retained without affecting or being affected by the synthesis of the first scaffolding protein in the cell. In addition, the protein that is intended to be bound and retained is preferably supplied from outside the cell also from the point that, to synthesize a large amount or multiple species of proteins inside the cell, the burden on the cell is important, sometimes affecting the growth capability.

To supply from outside the cell a protein that is intended to be bound and retained to the present artificial scaffolding material, bringing the present artificial scaffolding material and the protein into contact in a suitable aqueous medium. The protein may be supplied to an aqueous medium containing the present artificial scaffolding material, or the present artificial scaffolding material may be supplied into an aqueous medium containing the protein.

There are no particular limitations on the aqueous medium used in the supply step, as long as the biological activities of the cell constituting the present artificial scaffolding material and the protein that is intended to be bound and retained are preserved. The conditions under which these biological activities are preserved are conditions under which, regarding the protein and the cell, the biological activities thereof are also preserved after the adsorption step. For instance, it suffices to maintain a pH, an osmotic pressure and a temperature that are suitable for these. Although the pH may differ according to the protein and the cell, in general, it is in the range of pH 6 or greater but 9 or less. In addition, osmotic pressure is preferably approximately isotonic with respect to a cell such as a microorganism. Note that the osmotic pressure can be adjusted using suitable salts, in addition to buffering solution and isotonization agent. In addition, considering protein denaturation or the like, the temperature is preferably 1° C. or higher but 10° C. or lower, and more preferably 2° C. or higher but 5° C. or lower. As such aqueous medium, it may be saline solution or the like. For instance, it may be a tris hydrochloride buffer at on the order of 20 mM to 50 mM. In addition, it can also be an aqueous medium in which greater than 0 mM but 20 mM or less, more preferably 5 mM or greater but 15 mM or less, of calcium ions such as $CaCl_2$ solution are present. Furthermore preferably, it is an aqueous medium in which approximately 10 mM of calcium ions is present. For such calcium ion-containing aqueous medium, $CaCl_2$ aqueous solution can be cited typically. In such ionic environment, there is the tendency of the protein to be bound and retained onto the present artificial scaffolding material to become strong.

Regarding stirring of the aqueous medium, adjusting its intensity suitably is sufficient. Stirring conditions such as suitable stirring intensity can be determined by stirring under various stirring conditions the desired protein and the present artificial scaffolding material in an appropriate aqueous medium, and measuring the protein quantity and enzymatic activity of the cell fraction obtained as a result. Note that, to increase the contact frequency, increasing the supplied protein concentration is also effective.

Regarding preparation of the present complex material, a plurality of species of proteins may be supplied to the present artificial scaffolding material simultaneously, or they may be supplied sequentially. As the protein-binding domain that should be bound by the interaction domain of the protein that is intended to be bound and retained can be determined beforehand, when the protein-binding domains that are intended to be bound differ from one another, so they can be supplied simultaneously. On the other hand, for instance, if the protein-binding domains that should be bound are common, and in a case where a plurality of species of proteins is supplied simultaneously, controlling the amount of protein bound is sometimes difficult. Therefore, in such circumstance, if the amount of protein bound has been adjusted, the different proteins may be supplied sequentially.

In order to cause, through such a supply step, the protein-binding domain of the first scaffolding protein to bind and retain the protein that is intended to be bound and retained, it is desirable to stir the above aqueous medium. This is because the probability for both parties to make contact thereby increases.

The present complex material can be obtained by binding to the protein-binding domain the protein that is intended to be bound and retained.

(Recovery Step)

In order to recover the cell in which a cellulase and/or a cellulosome have been retained, it suffices to recover the microbe body fraction through solid-liquid separation of the aqueous medium by well known solid-liquid separation means. For instance, microorganism in which cellulase or the like has been retained can be recovered as a pellet by centrifugal separation.

The method for preparing the present complex material (the cellulase-holding material) of the present technique can be carried out in the above mode. Therefore, as described above, the cellulose degradation capability of the microorganism can be adjusted readily while providing a new solid phase carrier provided with a cellulase.

Note that the modes that have been already described regarding the present artificial scaffolding material and cell, first scaffolding protein and second scaffolding protein, which are constitutive element thereof, and the present complex material and constitutive elements thereof, can all be applied to the preparation method of the present technique.

(Method for Degrading Cellulose)

The method for degrading cellulose of the present technique can comprise a step of bringing cellulose, which is a cellulose series material, into contact with the present complex material that is binding and retaining one species or two or more species of cellulases, and degrading the cellulose with the cellulases. According to this degradation method, since one species or two or more species of cellulases are placed contiguously on the cell surface, cellulose can be degraded effectively. In this degradation method, the embodiments of various constitutive elements in the complex material for degrading cellulose can also be applied in the present technique. In particular, regarding degradation of cellulose, although the cooperative or stepwise action of a plurality of species of enzymes is necessary, cellulose series material can be degraded effectively according to the degradation method of the present technique.

(Method for Producing Useful Substance Using Cellulose)

The method for producing a useful substance using cellulose of the present technique can comprise a step of bringing the cellulose inside the cellulose series material into contact with the present complex material binding and retaining cellulase to degrade the cellulose, and a step of assimilating the cellulose decomposition product degraded by the cellulase with the cell of the complex material and converting it into a useful substance. According to this manufacture method, the cellulase bound and retained on the cell surface layer of the complex material can degrade cellulose in the cellulose series material while this cell can assimilate this decomposition product and convert it into a useful substance. Therefore, cellulose can be used effectively. In particular, even a cell that had difficulties using cellulose directly in prior art, can use cellulose and convert it into a useful substance. Note that the modes already described regarding the present complex material and cell, first scaffolding protein, second scaffolding protein, cellulase and the like, which are constitutive elements thereof, can all be applied also to the production method of the present technique. In addition, regarding the above degradation step, the modes described in the method for degrading cellulose series material can be applied directly.

In the production method of the present technique, as the cell, it is preferably a ethanol-producing microorganism. If it is an ethanol-producing microorganism, ethanol, which is useful as fuel, can also be produced directly from cellulose series material. In addition, as the cell, it can be an organic acid-producing microorganism such as of lactic acid.

Note that it suffices to carry out the degradation step to the conversion step in accordance with the cellulose series material and cell to be used, and the type of useful substance to be converted into. That is to say, it suffices to carry out the steps in accordance with the cells such as the microorganisms that produce the useful substance and the useful substance itself. For instance, the fermentation step, or the like, for conversion into useful substance such as ethanol or the like, can be carried out as follows. As culture medium, in addition to the above cellulose series material as carbon source, cellulose or oligosaccharides or monosaccharides generated from cellulose by a catabolic enzyme can be added as part of the carbon source. In so doing, efficiently assimilable monosaccharides can be supplied to microorganism in particular from the culture start time to the early stage of the culture. Note that, sugars are added to an extent that does not inhibit the catabolic enzyme, and preferably, sugars are added only for a defined period from the culture start time to the early stage of the culture (on the order of 2 to 10 hours from culture start). As nitrogen source and inorganic salts, those that are well known can be suitably selected and used.

In addition, for the culture, stationary culture, shaken culture or stirred aerated culture, and the like, can be used. The aeration condition can be suitably selected, synch as, under anaerobic conditions, under microaerobic condition and aerobic condition. There is also no particular limitation on the culture temperature, which can be in the range of 25° C. to 55° C., or the like. In addition, the culture time is also set as necessary, and can be in a range of 6 to 150 hours. In addition, pH adjustment can be carried out using inorganic or organic acid, alkaline solution, and the like. During culture, antibiotics such as ampicillin and tetracycline can be added to the culture medium, as necessary. Note that, after the transformation step has ended, the step of eliminating the microorganism from the culture solution to recover the fraction containing a useful substance such as ethanol, and furthermore, the step of concentrating this, can be carried out.

Note that, though there is no specific limitation to the useful substances, the useful substances may preferably be of a kind in which microorganisms can produce by using glucose.

For example, materials such as: lower alcohols such as ethanol, fine chemicals (such as coenzyme Q10, vitamins and their raw materials) with an application of addition of isoprenoid synthesis pathway, glyceline, plastic and chemically synthetic materials that can be materialized by the bio-refinery techniques may be employed. Further, though no specific limitation is cast upon the microorganisms that use glucose, the microorganism for example may be modified to be able to produce chemical compounds that are not the inherent metabolite by substitution or addition of one species or two or more species of enzymes of glucose metabolic system through genetic engineering.

Hereinafter, the present technique will be described concretely giving examples; however, the present technique is not limited in any way by these examples, and can be carried out in a variety of modes without departing from the scope of the present invention.

EXAMPLE 1

Figure 3:
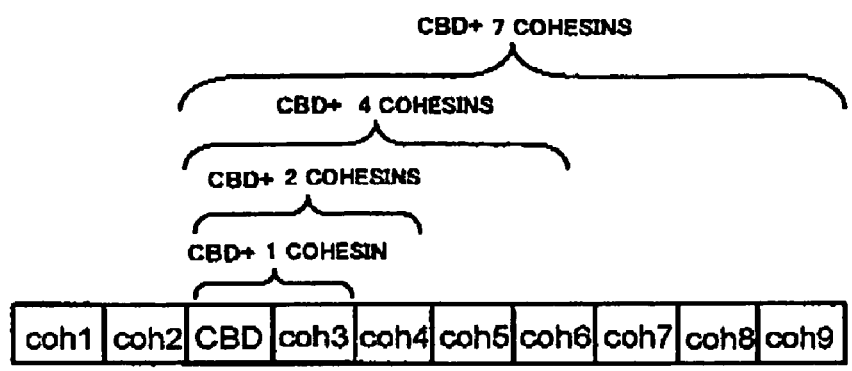
FIG. 3 shows the structure of the Type I scaffolding protein gene used in the present example.

Acquisition DNA Fragments Coding for the First Scaffolding Protein and the Second Scaffolding Protein In the present example, cloning of a DNA fragment coding for a scaffolding protein derived from *Clostridium thermocellum* (*C. thermocellum*; hereinafter may be simply called Ct) was carried out. First, the genome was extracted from Ct ATCC27405. The structure of the CipA gene coding for the CipA protein (NCBI home page, Accession No.: L08665), which is a Type I scaffolding protein (corresponding to the first scaffolding protein of the present invention), is shown in FIG. 3. For this CipA gene, DNA fragments containing each portion of the genome such as those shown in FIG. 3 (each portion of CBD (cellulose-binding domain)+one Type I cohesin (Coh3), two (Coh3 and 4) and seven (Coh3 to Coh9)) were synthesized. That is to say, based on the DNA sequences of each portion of these genomes (the database and Accession No.), suitable primers were designed and various DNA fragments were acquired via amplification by the PGR method according to the art. In addition, regarding the portion CBD+ four Type I cohesins (Coh3 to Coh6) in the same gene was acquired by gene synthesis. Note that, regarding the DNA fragment provided with seven Type I cohesins, Type II dockerin has been retained.

In addition, based on the DNA sequence of the SdbA gene coding for the Type II cohesin of this Ct ATCC27405 (NCBI home page, Accession No.: U49980), DNA fragments coding for a Type II anchor protein provided with one and two Type II cohesins respectively (corresponding to the second scaffolding protein of the present invention) were also acquired similarly by the PCR method according to the art.

EXAMPLE 2

Synthesis of Endoglucanase in a Cell-Free System

In the present example, from the genome of Ct ATCC27405, suitable primers were designed based on the DNA sequence of the CelA gene, which is an endoglucanase gene (NCBI home page, Accession No.: K03088), after amplification by the PCR method according to the art, a CelA gene fragment was cloned. Note that the CelA gene has at the C-terminal side thereof a Type I dockerin which is an interaction domain with Type I cohesin. The cloned CelA gene fragment was inserted into a pET-23b vector (Novagen), the region from the T7 promoter to the terminator containing the CelA gene was amplified by the PCR method, to serve as the template in a cell-free synthesis. Synthesis of CelA was carried out by reaction in a cell-free solution, at 25° C., for five hours. Note that the cell-free synthesis was carried out using the WAKO PURE system (manufactured by Wako Pure Chemical Industries), according to the protocol thereof.

EXAMPLE 3

Expression of the First Scaffolding Protein or the Second Scaffolding Protein on the Yeast Surface Layer In the present example, each gene fragment acquired in Example 1 was inserted into the pYD1 vector (Invitrogen) in a form that added a His-tag at the respective C-termini, and these were used to carry out transformation of the yeast *S. cerevisiae* EBY100. Each transformed strain was cultured using a YNB+0.5% casamino acid+2% glucose culture medium, at 30° C., when OD600=2 was exceeded, the yeast was harvested, then, was used to inoculate a YNB+0.5% casamino acid+2% galactose culture medium so as to obtain OD600=0.5, and induced expression was carried out at 30° C. for 48 hours. Thereafter, 1 ml of fungal body at OD600=1, was washed with 1 ml of PBS, and suspended in 125 µl of PBS. To this suspension, 0.5 µg of anti-His-tag antibody as the primary antibody and 1 mg/ml final concentration of BSA were added, the suspension was left to stand in ice for 30 minutes, and suspended from time to time. Next, the fungal body was centrifuged, washing with 1 ml of PBS was performed, [the fungal body] was suspended in 125 µl of PBS, 0.5 µg of Cy5 labeled anteing-G antibody as the secondary antibody and 1 mg/ml final concentration of BSA were added, the suspension was left to stand in ice for 30 minutes, and suspended from time to time. Thereafter, the fungal body was centrifuged, washing with 1 ml of PBS was performed, the fungal body was suspended in 50 μl of PBS, and the fluorescence of Cy5 was measured under a fluorescence microscope. The result is shown in FIG. 4.

Figure 4:
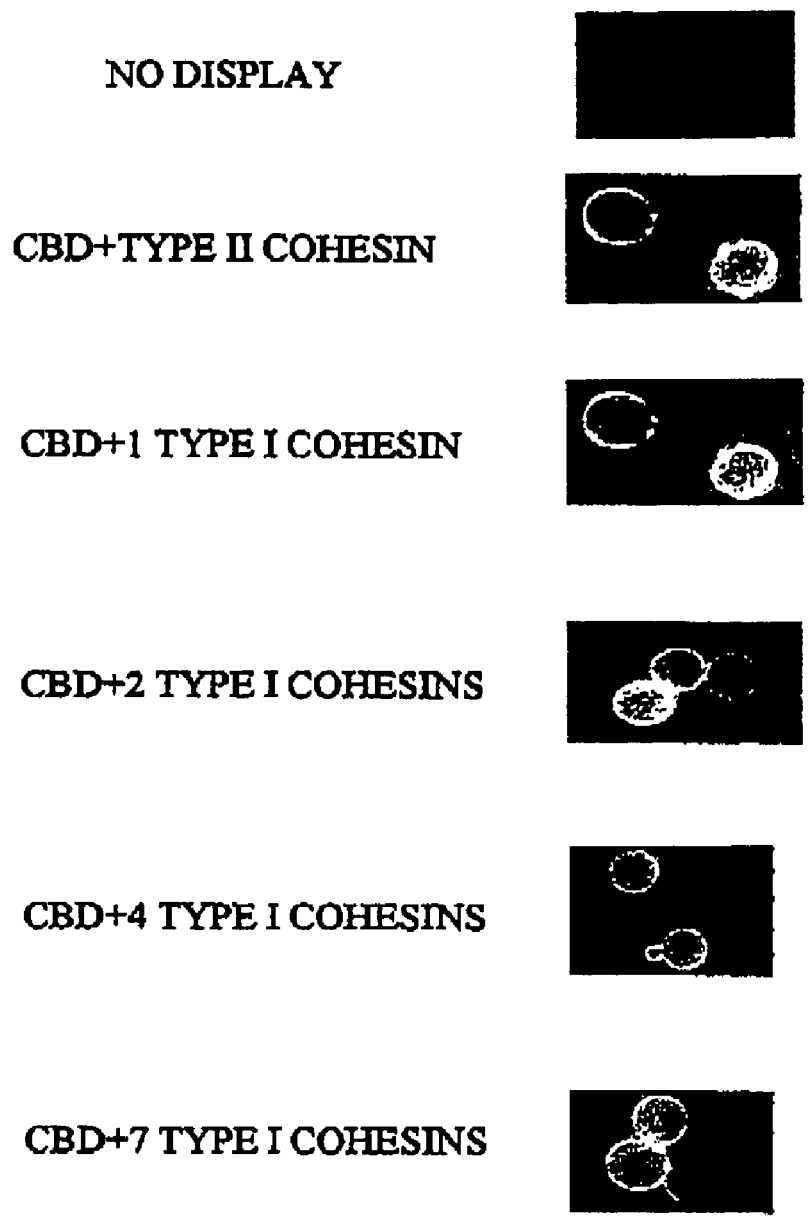
FIG. 4 shows the state of expression in yeast of various scaffolding protein of the examples.

As shown in FIG. 4, for all the Type I cohesin protein gene fragments and Type II cohesin protein gene fragments, fluorescence was observed uniformly over the entire surface of cells caused to express the fusion protein coded by the fragments. From this, it was shown that the scaffolding protein and anchor protein coded by each gene fragment was expressed sufficiently in the surface layer of yeast.

EXAMPLE 4

Supply and Retention of Endoglucanase to Yeast Displaying the First Scaffolding Protein on the Surface Layer In the present example, endoglucanase CelA synthesized by cell-free system in Example 2 was supplied externally to the yeast displaying one Type I cohesin in Example 3, to confirm the function of the scaffolding protein. Using 1 ml of CBD+ one Type I cohesin-displaying yeast at OD600=5, washing with 20 mM Tris-HCl pH8.0, 10 mM $CaCl_2$ followed by blocking operation with a solution of 20 mM Tris-HCl pH8.0, 0.15M NaCl, 10 mM $CaCl_2$ and 10 mg/ml BSA at 4° C. for 1 hr were carried out; after washing three times with a solution of 20 mM Tris-HCl pH8.0, 0.1M NaCl, 10 mM $CaCl_2$ and 0.05% tween 20, the yeast was mixed in a solution of 20 mM Tris-HCl pH8.0, 0.15M NaCl, 10 mM $CaCl_2$ and 10 mg/ml BSA with 50 μl of CelA cell-free synthesis solution, and reaction was carried out at 4° C. for one hour. Next, washing was performed four times with a solution of 20 mM Tris-HCl pH8.0, 0.1M NaCl, 10 mM $CaCl_2$ and 0.05% tween 20, yeast with CelA bound was mixed to a solution of 1% CMC, 20 mM acetic acid buffer pH6.0, and 10 mM $CaCl_2$, and reaction was carried out at 60° C. This reaction solution was measured for CMC degradation activity by the TZ-assay method. Note that, as a control, yeast S. cerevisiae EBY100 not displaying any protein was supplied similarly with CelA and manipulated similarly. These results are shown in FIG. 5.

Figure 5:
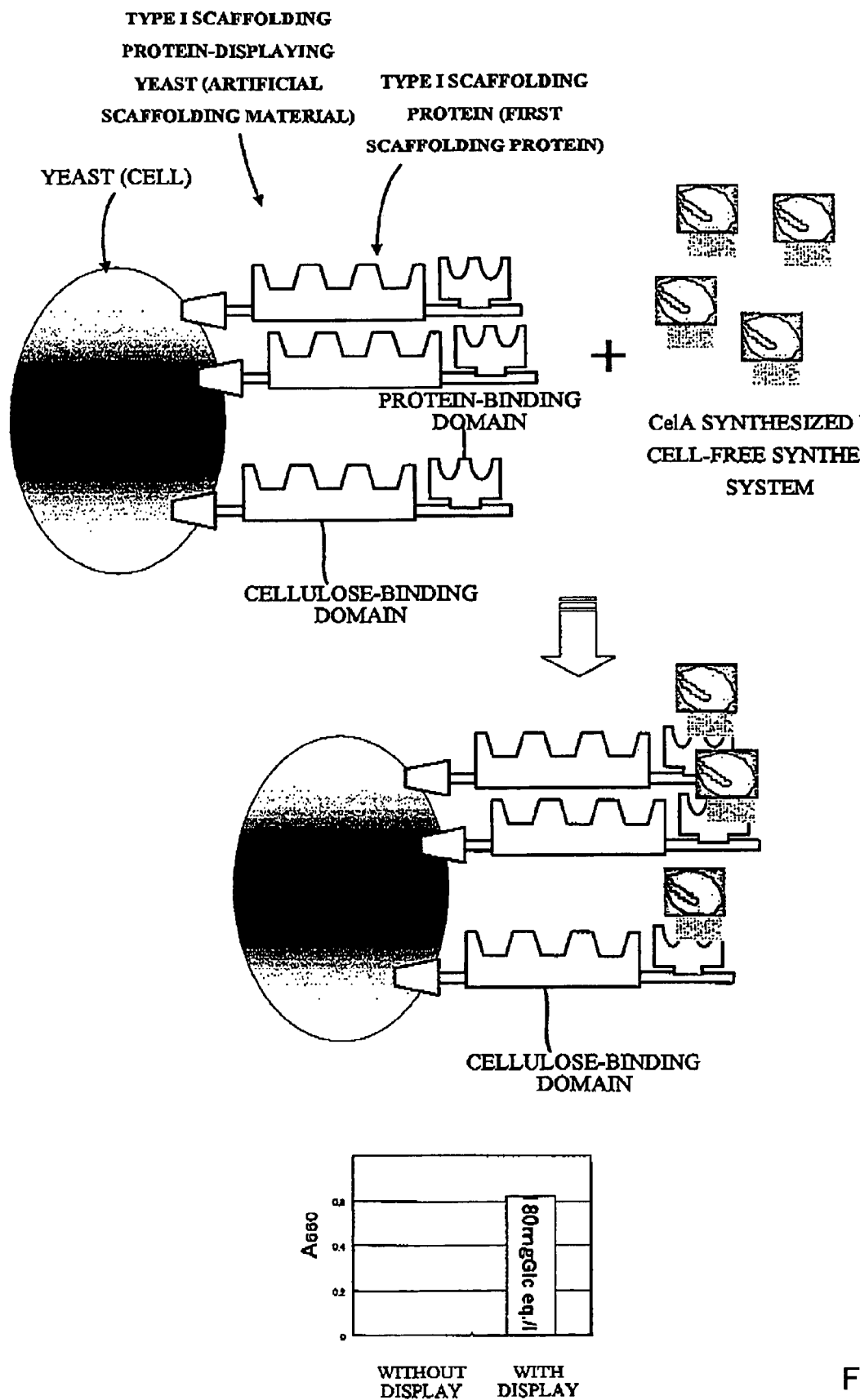
FIG. 5 shows the relationship between CelA and scaffolding protein-expressing yeast in the examples, and graph showing the CMC degradation activity of yeast that bound and retained CelA.

As shown in FIG. 5, CMC degradation activity was observed in Type I cohesin-displaying yeast, showing that CelA was bound to Type I cohesin. That is to say, in the displaying yeast, Type I cohesin was shown to be displayed on the surface layer functionally; while CelA bound thereto was functioning. In contrast to this, in yeast not displaying any protein, CMC degradation activity by CelA was not observed. In addition, when CelA was similarly supplied to other Type I cohesin-displaying expressing yeasts for which Cy5 fluorescence was observed, CMC degradation activity was observed.

From these results, it was revealed that, when Type I cohesin is displayed on the surface layer of yeast cell, by supplying cellulase from outside of this yeast, cellulase such as endoglucanase derived from cellulosome can be bound to Type I cohesin and retained. As various cellulases derived from cellulosome are provided with Type I dockerin, which is an interaction domain to Type I cohesin, a protein can be supplied in this way from outside the cell and selectively bound and retained on Type I cohesin. Therefore, it was revealed that a multitude and/or multiple species of proteins such as enzymes could be provided on the cell surface layer, without imposing on the cell the burden of synthesizing such protein, such as genetic modification and biosynthesis of heterologous protein.

EXAMPLE 5

Aggregation Properties of Yeast Displaying on the Surface Layer the First Scaffolding Protein In the present example, aggregation properties were determined for yeasts displaying Type I scaffolding protein on the surface layer. With respect to yeast S. cerevisiae EBY100 displaying on the surface layer CBD+ one, two, four and seven TypeI cohesins respectively, 72 hours after induced expression, 10 ml of each culture solution (note that the culture medium was the culture medium at the time of induction: YNB+0.5% casamino acid+2% glucose culture medium) was recovered in a test tube, thoroughly suspended, then, was left to stand for five minutes. Aggregation properties were also determined similarly for S. cerevisiae EBY100 not displaying any protein. The result is shown in Table 3.

TABLE 3

| | No. of Type 1 cohesins displayed | | | | |
|---|---|---|---|---|---|
| | NO DISPLAY | ONE | TWO | FOUR | SEVEN |
| Aggregation properties | − | − | − | ++ | + |

As shown in Table 3, although aggregation properties were not observed in the non-displaying yeast, aggregation properties were visually confirmed in each yeast expressing four and seven Type I cohesins. Among these, stronger aggregation properties were confirmed in the yeast expressing four Type I cohesins. From this result, it was thought that aggregation properties could be conferred to a cell provided with three or more Type I cohesins on the surface layer. Note that, aggregation properties were not confirmed particularly for yeast S. cerevisiae EBY100 not displaying proteins. Taking into consideration the surface layer expression state of each protein observed in Example 2, it was thought that, as a result of providing a tandem repeat of a given number of Type I cohesins or more, the density of Type I cohesin on the cell surface layer became high, resulting in the cells aggregating.

EXAMPLE 6

Figure 6:
FIG. 6 shows the state of Type II cohesin expression in Type II cohesin-expressing yeast in the example.
Figure 6:
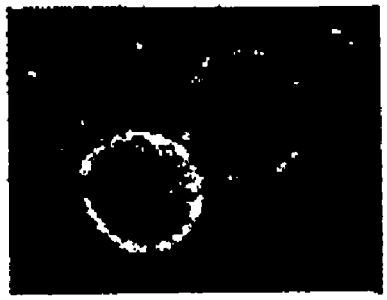

Coexpression of the First Scaffolding Protein and the Second Scaffolding Protein on the Yeast Surface Layer First, the surface layer display of one Type II cohesin in the SdbA gene of Ct ATCC27405, which is a the second scaffolding protein, was carried out with yeast (S. cerevisiae) MT8-2. First, based on the DNA sequence of the SdbA gene of Ct ATCC27405 (NCBI home page, Accession No.: L08665), a DNA fragment coding for a fusion protein fused on the C-terminal side of Type II cohesin with SAG1, which is a yeast surface layer binding domain, and a His-tag on the N-terminal side, was acquired. For this DNA fragment, a vector for chromosomal insertion was constructed, and this vector for chromosomal insertion was used to introduce the DNA fragment containing one Type II cohesin into yeast chromosome. The yeast after introduction operation was cultured in YPD culture medium for 24 hours, and fluorescence staining using His-tag was carried by the method indicated in Example 3. The result was, as shown in FIG. 6, fluorescence was displayed on the cell surface layer, confirming the expression of Type II cohesin in the surface layer.

Next, coexpression of CBD+ Type I cohesin and Type II cohesin was carried out with yeast (*S. cerevisiae*) MT8-2. First, for each of CBD+ one Type I cohesin (Coh3) and CBD+ two Type I cohesins (Coh3 and Coh4), which are first scaffolding proteins, a DNA fragment coding for a fusion protein, in which AGA2 and Xpress-tag have been fused on the N-terminal side and the Type II dockerin sequence has been fused on the C-terminal side, was acquired. Note that the DNA sequence of CtCipA DocII, the Type II dockerin of CtCipA, is disclosed in the CipA gene (NCBI home page, Accession No.: L08665), and the DNA fragment was acquired based on these sequences.

Yeast surface layer display was carried out using this DNA fragment and the previously-acquired DNA fragment in which SAG1 and His-tag were fused to Type II cohesin. That is to say, the DNA fragment CBD+ Type I cohesin (one or two)+ Type II dockerin was introduced in a 2µ vector, and this vector was introduced in the already prepared yeast MT8-2 displaying Type II cohesin on the surface layer. Transformed yeast was cultured in SD-ura culture medium for 72 hours, then, fungal body staining was carried out using anti-X-press antibody as primary antibody, by the method indicated in Example 3.

Figure 7:
FIG. 7 shows the state of expression of Type II cohesin in Type I cohesin+Type II cohesin-expressing yeast in the example.
Figure 7:
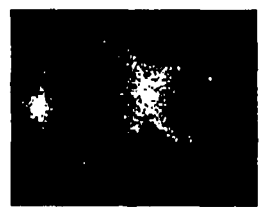
Figure 7:
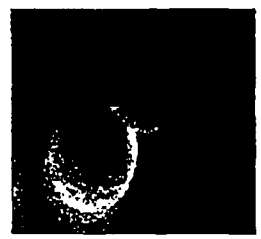

The result is shown in FIG. 7.

As shown in FIG. 7, fluorescence was observed in strains caused to coexpress Type I cohesin and Type II cohesin, second protein having Type II cohesin was observed to be surface layer displayed on the yeast surface layer, at the same time as a scaffold was reconstituted, in which Type II dockerin of the first scaffolding protein was bound to of the Type II cohesin of this second scaffolding protein.

In addition, CtCelA expressed in a cell-free system similarly to Example 4 was supplied to the strain expressing Type II cohesin only and to the strain coexpressing Type II cohesin and Type I cohesin, to measure the activity of degrading 1% CMC. The result is shown in FIG. 8.

Figure 8:
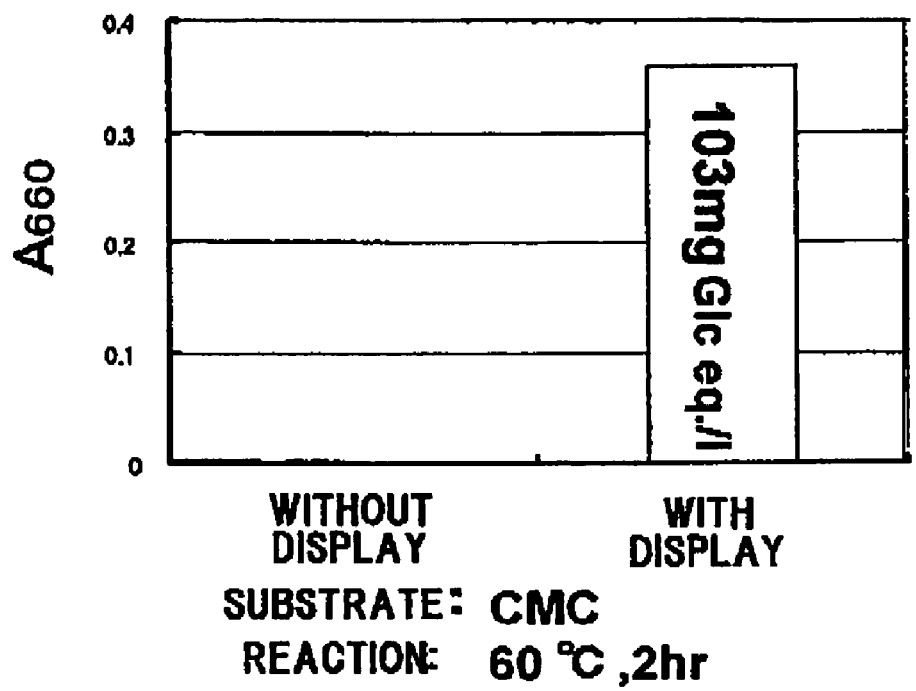
FIG. 8 shows CMC degradation activity of Type I cohesin+Type II cohesin-expressing yeast in the example.

As shown in FIG. 8, significant CMC degradation activity was displayed only in the coexpressing yeast.
From this result, it was revealed that an enzyme complex material could be constructed, in which an enzyme having Type I dockerin is bound and retained by an artificial scaffold comprising Type I cohesin and Type II cohesin on the yeast surface layer.

EXAMPLE 7

In the present example, yeasts respectively displaying one, two, four and seven Type I cohesins in Example 3 were supplied from the outside thereof with endoglucanase CelA, which was synthesized by cell-free system similarly to Example 4, and the CMC degradation activity was measured over time. Similarly to Example 4, yeast EBY100 not displaying any protein was used as a control and manipulated similarly. The CMC degradation activity is shown in FIG. 9 along with the reaction time course.

Figure 9:
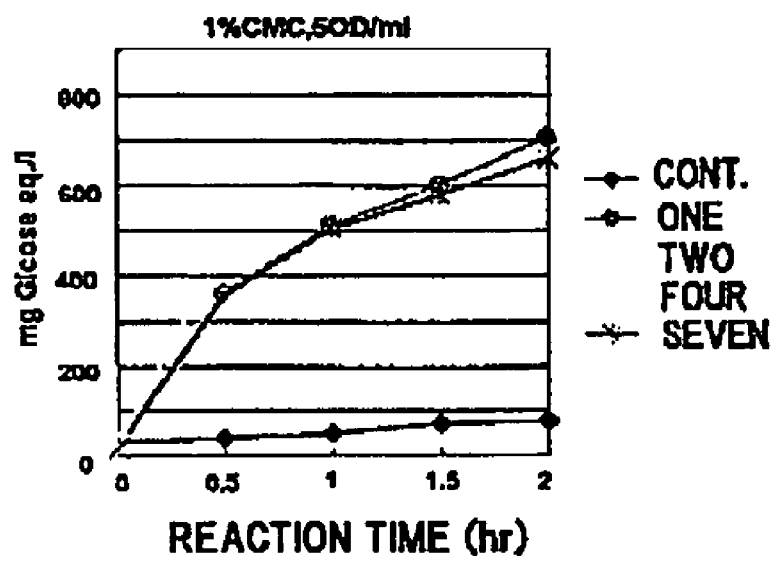
FIG. 9 shows time course of CMC degradation activity in yeast that bound and retained CelA via Type I cohesin in the example.

As shown in FIG. 9, similarly to Example 4, CMC degradation activity was confirmed for the yeast that retained the first scaffolding protein retaining the Type I cohesin, while at the same time, it was revealed that the CelA was functioning relatively to the number of Type I cohesins the first scaffolding protein retains. The yeast displaying the first scaffolding protein displaying one Type I cohesin exerted clear CMC degradation activity with respect to the control. In addition, an increase in activity of approximately 20% in the initial rate was observed in the yeasts that displayed two and four Type I cohesins respectively, compared to the yeast displaying one identical domain. Note that, regarding the yeast displaying seven Type I cohesins, an increase in the CMC degradation activity according to the number of cohesins was not particularly observed.

In addition, using 1 ml of these Type I cohesin yeasts at OD600=10 after supplying CelA, enzymatic reactions were carried out with 0.5% phosphoric acid-swollen cellulose as substrate, at 50° C. for 40 hours. The result for the yeast displaying the first scaffolding protein, which holds four Type I cohesins, is shown in FIG. 10.

Figure 10:
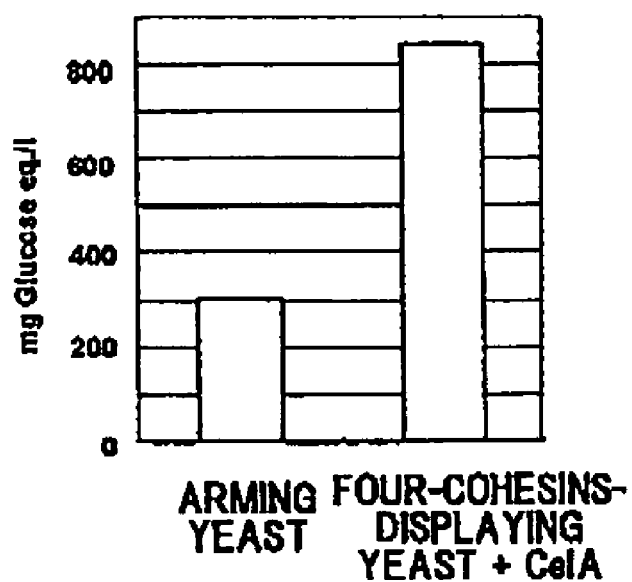
FIG. 10 shows phosphoric acid-swollen cellulose degradation activity of yeast that bound and retained CelA by displaying on the surface layer four Type I cohesins in the example.

As shown in FIG. 10, the activity of degrading 0.5% phosphoric acid-swollen cellulose was confirmed, revealing that CelA is bound to Type I cohesin. Note that in FIG. 10, when comparison was made with the amount of phosphoric acid-swollen cellulose degraded by prior art aiming yeast (article by Fujita. Y., et al., Appl. Environ. Microbiol., 70 (2), 1207-1212 (2004)) and endoglucanase, higher degradation activity was shown by four Type I cohesins-displaying yeast.

EXAMPLE 8

Type I Cohesin Enzyme Contiguity Effect

Figure 11:
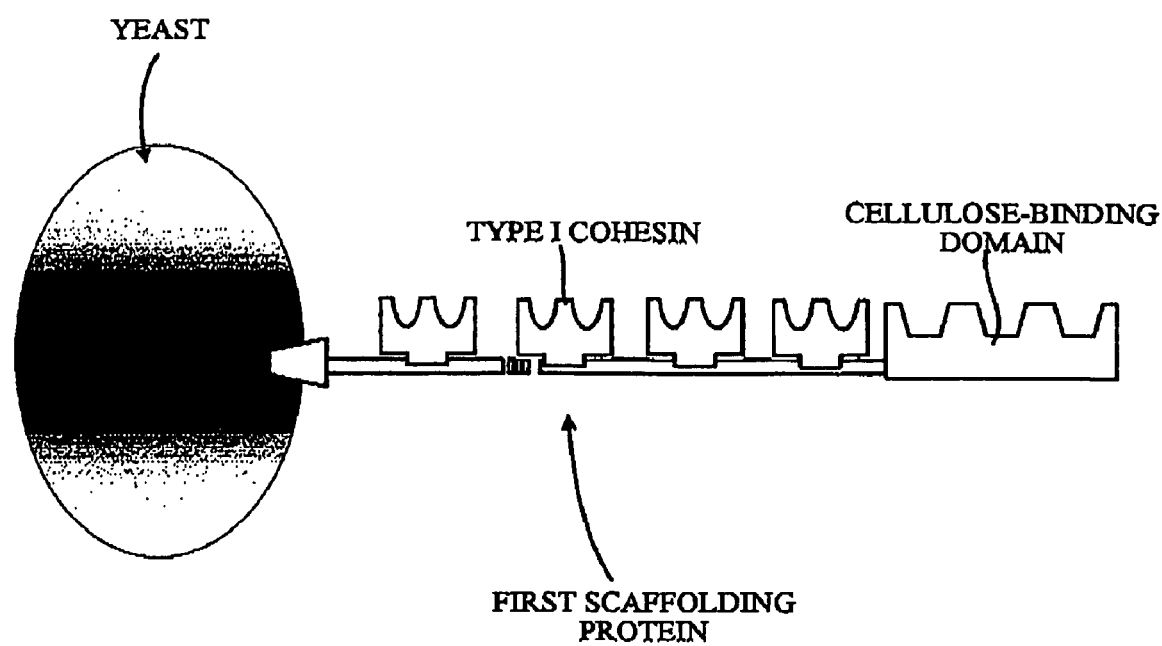
FIG. 11 shows the surface layer display state of cellulose-binding domain and Type I cohesins (four) in the example.

With Example 3 as reference, pYD1 vector was modified so that the target protein was on the N-terminal side to prepare the pYD5 vector. With this vector, the cellulose-binding site CBD was placed on the outermost side, allowing Type I cohesin to be displayed more toward the yeast surface layer side from it (refer to FIG. 11). The first scaffolding protein retraining CBD+ four Type I cohesins was introduced in an expressible manner into the present vector, as shown in FIG. 11. According to Example 3, *S. cerevisiae* EBY100 was transformed using this vector to display the above first scaffolding protein on the yeast surface layer.

Endoglucanases CelA and CelD, which were cell-free synthesized, were bound respectively alone to the yeast displaying four Type I cohesins and a cellulose-binding site according to the methods described in Example 3, to prepare CelA-displaying yeast and CelD-displaying yeast. These two species of yeast were measured, according to the methods described in Example 7 for the activity of degrading 0.5% phosphoric acid-swollen cellulose. Furthermore, the amounts of CelA and CelD added were respectively halved, and these two species were bound to the four Type I cohesins-displaying yeast to prepare a (CelA+CelD)-displaying yeast. This yeast was also measured for the activity of degrading 0.5% phosphoric acid-swollen cellulose. These results are shown together in FIG. 12.

Figure 12:
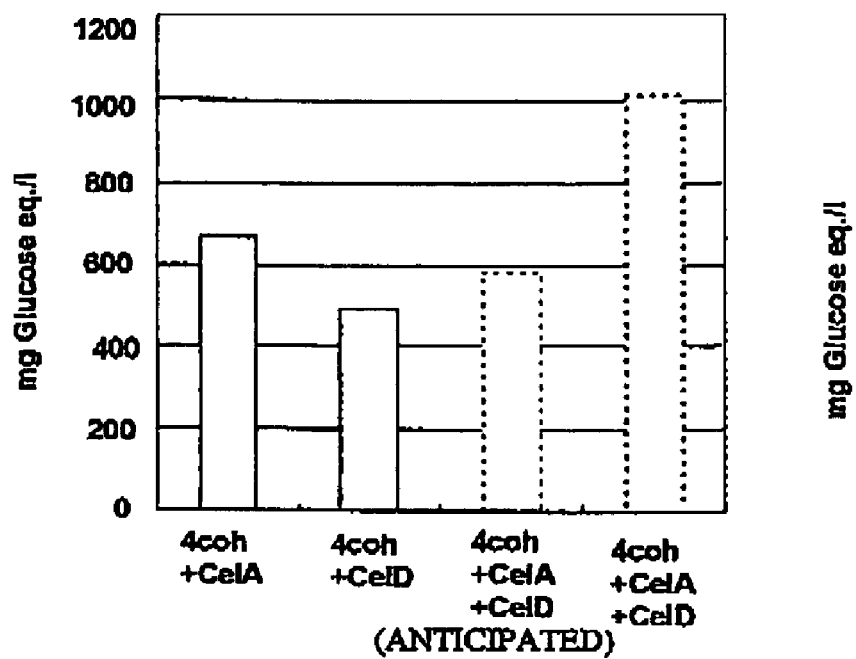
FIG. 12 shows a graph comparing phosphoric acid-swollen cellulose degradation activities of CelA-displaying yeast, CelD-displaying yeast and (CelA+CelD)-displaying yeast in the example.

As shown in FIG. 12, CelA-displaying yeast and CelD-displaying yeast respectively showed satisfactory phosphoric acid-swollen cellulose degradation activity. In addition, (CelA+CelD)-displaying yeast showed a degradation activity that was 1.7 times higher than (CelA-displaying yeast degradation activity and CelD yeast degradation activity)/2. From the above result, (CelA+CelD)-displaying yeast has higher phosphoric acid-swollen cellulose degradation activity than displaying CelA and CelD respectively alone, and a synergistic effect of CelA and CelD became clear. In the present example, it was found that, by CelA and CelD being placed contiguously by binding of CelA and CelD to Type I cohesin, these enzymes respectively had synergistic action on the phosphoric acid-swollen cellulose degradation activity.

EXAMPLE 9

Phosphoric Acid-Swollen Cellulose Degradation Capability of Yeast Displaying Cohesin on the Surface Layer and Endoglucanase CelA In the present example, a genetic recombinant yeast displaying cohesin on the cell surface layer was created and the cellulose degradation capability when cellulase was supplied to this yeast was compared with parental strain yeast not displaying cohesin. Concretely, a DNA fragment was created, in which DNA having a coding region downstream of the HOR7 promoter containing CBD and four cohesins from the CipA gene coding for the CipA protein of Ct (NCBI home page, Accession No.: L08665) and AGA2 gene fused on the downstream side of this coding region, corresponding to the C-terminus of the amino acid sequence. This DNA fragment was introduced according to conventional methods into the chromosome of a yeast in which AGA1 is expressed with the HOR7 promoter (parental strain: BY4741), which became a cohesin-displaying yeast Cohesin-displaying yeast, CelA-secreting yeast and normal yeast (BY4741 strain) were precultured in test tubes, then, were respectively cultured for 36 hours in 2 L baffled flasks.

Figure 13:
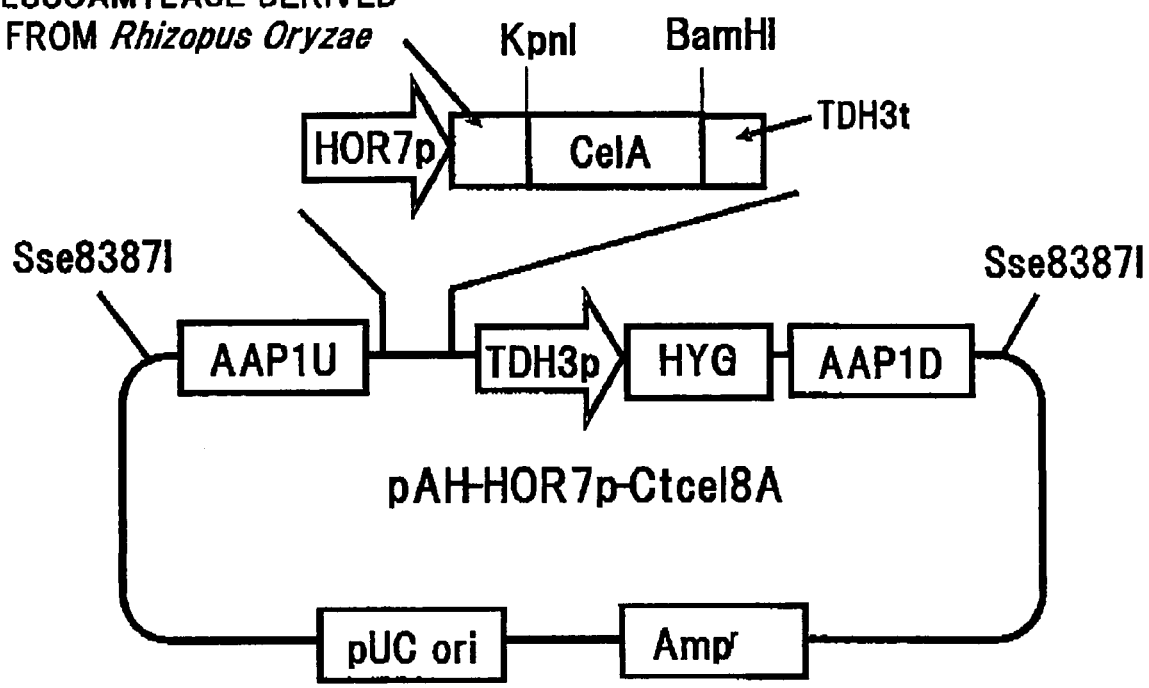
FIG. 13 shows a structure of vector for preparing a Cel A secreting yeast.

Note that the above CelA yeast was prepared as follows. The vector pAH-HOR7p-Ctce18A was prepared to introduce the cellulase into a chromosome. As illustrated in FIG. 13, the sequence from 3000 bp to 2000 bp upstream of the AAP1 gene (hereinafter, referred to as AAPIU) was cloned from the genomic DNA of Saccharomyces S288C by PCR reaction. In addition, the sequence from −2000 bp to −1000 bp upstream of the AAPI gene (hereinafter, AAPID) from the genomic DNA of S288C was cloned by PCR. In addition, as a marker for confirmation of vector gene introduction, a TDH3 promoter (TDH3p) and a CYC3 terminator (CYC1t) were linked to a hygromycin resistance gene. A DNA fragment having the coding DNA of the signal peptide of glucoamylase derived from Rhizopus oryzae, Ct Cel A coding DNA (in between Kpn I and Bam HI) and TDH3 terminator under control of the HOR7 promoter was prepared. Then, the DNA fragment was introduced to downstream of the AAPIU and consequently pAH-HORp-Ctce18A was constructed. This was cut with SseI8387I, linearized, and introduced into the yeast chromosome according to conventionally procedure.

Two types of enzyme-yeast complexes were prepared by collecting 80 ml of supernatant of CelA secreting-producing yeast as a CelA solution, mixing respectively the cohesin-displaying yeast and the parental strain to 80 ml of CelA solution in the presence of 10 mM of calcium chloride so as to obtain OD600=30, and shaking at 25° C. and 40 rpm for approximately 3 hours.

The yeast-enzyme complex was mixed so as to obtain a final phosphoric acid-swollen cellulose concentration of 0.2%, and shaken culture was carried out at 55° C. and 40 rpm for approximately 20 hours. Thereafter, each solution was recovered, centrifugal separation was carried out, and the amount of reducing sugar in the centrifugation supernatant was measured by the Somogyi-Nelson method. The result is shown in FIG. 14.

Figure 14:
FIG. 14 shows a graph showing phosphoric acid-swollen cellulose degradation activity of yeast that bound and retained CelA by displaying on the surface layer four Type I cohesins in the example.

As shown in FIG. 14, it was revealed that the phosphoric acid-swollen cellulose degradation capability of the complex of cohesin-displaying yeast, which displays cohesin and CBD on the cell surface layer, and the CelA was approximately 3.2 times higher compared to the normal yeast, which does not form a complex.

From the above, it was revealed that a remarkably high cellulose degradation capability could be exerted even with the same amount of cellulase by co-localizing a yeast that expressed scaffold proteins on the surface layer.

EXAMPLE 10

Verification of β-Glucosidase (BGL) Coexpression Effect in Scaffolding Protein Expression Yeast Similarly to Example 9, a DNA fragment was prepared, coding for a fusion protein containing CBD and a four cohesins gene downstream of the HOR7 promoter and downstream side thereof a further AGA2 gene. This DNA fragment was introduced according to conventional methods into the chromosome of the yeast BJ-AGA1 (parental strain: BJ5465), in which the AGA2 gene is expressed via the HOR7 promoter, to prepare a modified yeast BJ004 displaying on the surface layer the above fusion protein through AGA1 and AGA2.

BGL is not present in cellulosome constituting enzymes. Therefore, cellulose degradation products degraded by the cellulosome, cannot be assimilated as-is by the yeast Saccharomyces cerevisiae. Therefore, BGL was displayed on the yeast surface layer. That is to say, in order to display a BGL derived from A. aculeatus (NCBI home page, Accession No.: D64088) on the yeast surface layer the BGL gene was fused to the SAG1 gene and inserted downstream of the HOR7 promoter according to conventional methods, then introduced into the chromosome of the BJ004 strain according to conventional methods, to obtain a scaffolding protein-BGL expressing yeast BJ104, CelA derived from Clostridium thermocellum synthesized by cell-free synthesis was supplied to and adsorbed onto yeast BJ104 strain, then mixed with a 1% CMC solution, then degradation test was carried out at 60° C., and the amount of reducing sugar was measured by the TZ method (detection wavelength: 660 nm). The result is shown in FIG. 15.

Figure 15:
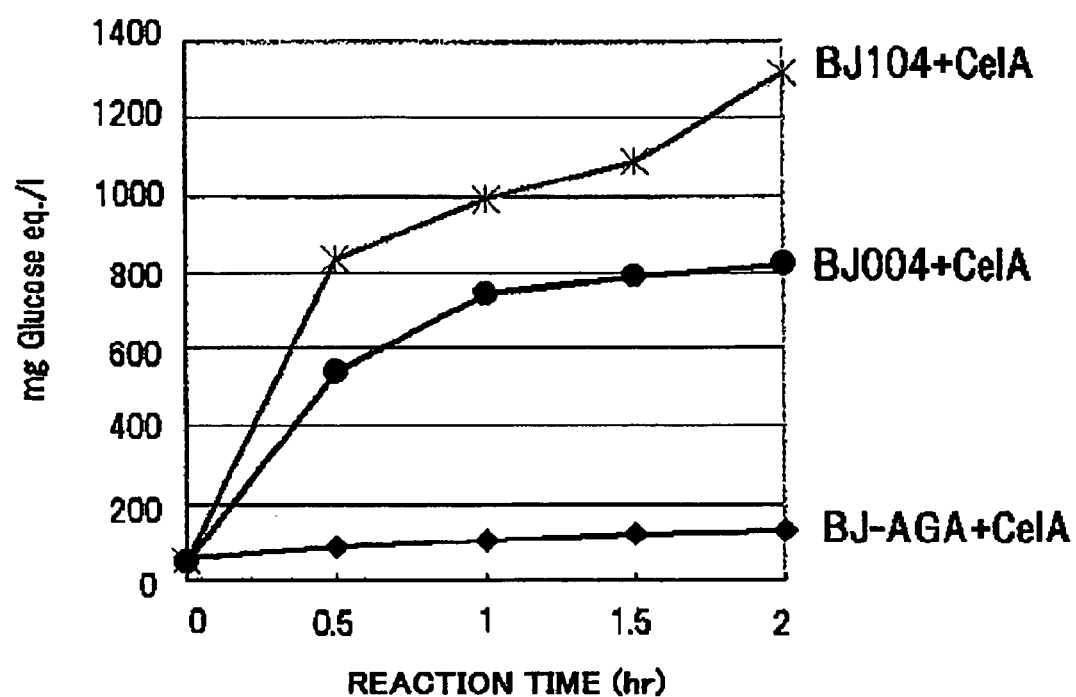
FIG. 15 shows a graph showing CMC degradation activities of fi-glucosidase (BGL) and scaffolding protein coexpressing yeast BJ104 (+cell-free synthesized Cel A) in the example.

As shown in FIG. 15, yeast BJ104 retaining endoglucanase and β-glucosidase on the scaffolding protein reached approximately 1.6 times the cellulose degradation capability of the yeast BJ004 without β-glucosidase introduction. From the above, it was revealed that a plurality of species of enzymes required to degrade cellulose could be retained efficiently against the scaffolding protein material, this resulting in allowing the cellulose degradation efficiency to be increased remarkably.

EXAMPLE 11

Ethanol Preparation by the Cellulosome-Reconstituting Yeast (BJ104pA strain)

In the present example, CelA derived from Clostridium thermocellum (DNA sequence of the CelA gene (NCBI home page, Accession No.: K03088)) was introduced using the 21 plasmid into the yeast BJ104 strain displaying on the cell surface layer a scaffolding protein material to prepare the cellulosome-reconstituting yeast BJ104pA strain. This strain was cultured in the SD-Ura culture medium for 24 hours, then, was cultured further in SD-Ura+2% CAA (casamino acid) culture medium for 24 hours. After harvesting 1 ml of fungal body at 10 OD, washes were performed twice with 20 mM tris hydrochloride buffer solution (pH 8.0) in the presence of 10 mM of calcium chloride, and the 1% CMC degradation test was carried out at 60° C. The result is shown in FIG. 16.

Figure 16:
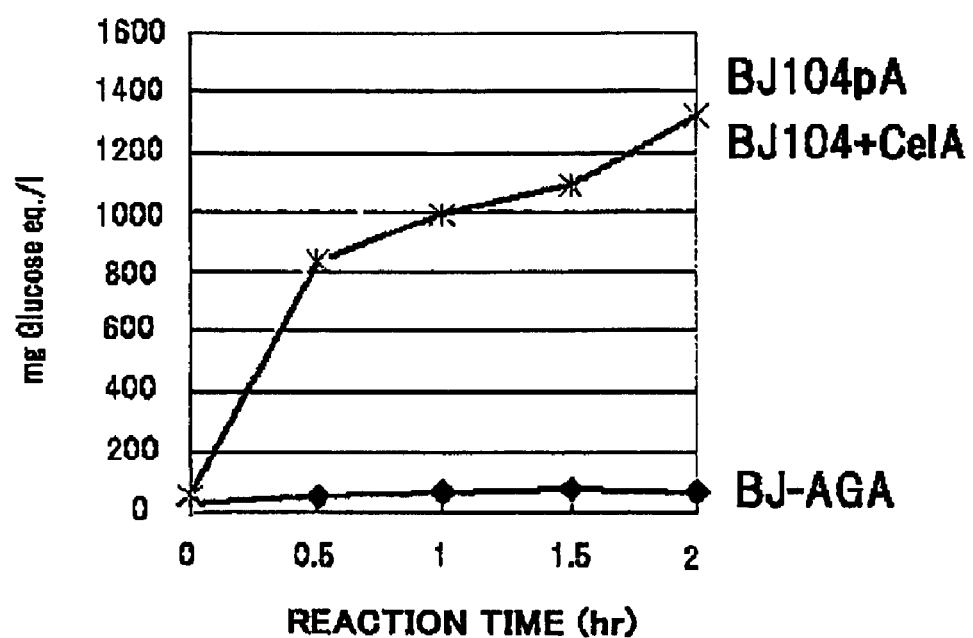
FIG. 16 shows a graph showing CMC degradation activities of cellulosome-reconstituting yeast BJ104pA autonomously producing scaffolding protein, β-glucosidase (BGL) and Cel A in the example.

As shown in FIG. 16, cellulosome-reconstituting yeast BJ104pA reached a similar cellulose degradation activity to the yeast BJ104 strain, which retained cell-free synthesized celA on the scaffolding proteins. In addition, BJ104 strain (no supply/retention of CelA) and BJ104pA strain were used, respectively mixed with 0.5% phosphoric acid-swollen cellulose, and reacted at 45° C. for 48 hours, then, the ethanol concentration in the reaction solution was measured. As a result, 0.23 g/l of ethanol was detected only in BJ104pA.

From the above, it was revealed that by secretion and expression of endoglucanase and β-glucosidase in yeasts retaining a scaffolding protein material on the cell surface layer, the endoglucanase could be held by the scaffolding protein retention material.

What is claimed is:

1. An artificial scaffolding material for retaining proteins, the artificial scaffolding material comprising:
   a cell; and
   first scaffolding proteins attached to the surface of said cell, said first scaffolding proteins comprising a plurality of cohesin domains of a cellulosome capable of non-covalently binding one or more species of proteins with compatible dockerin domains and arranged in tandem to confer aggregation properties to said cell,
   wherein said first scaffolding proteins are exogenous to said cell.

2. The artificial scaffolding material according to claim 1, wherein at least one of said cohesin domains is a Type I cohesin domain.

3. The artificial scaffolding material according to claim 1, wherein at least one of said first scaffolding proteins contains a cellulose-binding domain.

4. The artificial scaffolding material according to claim 1, wherein at least one of said first scaffolding proteins is a cellulosome scaffolding protein.

5. The artificial scaffolding material according to claim 4, wherein said cellulosome scaffolding protein is from *Clostridium thermocellum*.

6. The artificial scaffolding material according to claim 1, wherein at least one of said first scaffolding proteins comprise three or more of said cohesin domains.

7. The artificial scaffolding material according to claim 6, wherein at least one of said first scaffolding proteins comprise four or more but seven or less of said cohesin domains.

8. The artificial scaffolding material according to claim 1, wherein said cell expresses said first scaffolding proteins.

9. The artificial scaffolding material according to claim 1, further comprising a second scaffolding protein attached to the surface of said cell, said second scaffolding protein comprising a plurality of cohesin domains of a cellulosome,
   each of said first scaffolding proteins comprising a dockerin domain of a cellulosome capable of binding to one of said cohesin domains of said second scaffolding protein via a non-covalent bond,
   wherein said second scaffolding protein is exogenous to said cell.

10. The artificial scaffolding material according to claim 9, wherein said second scaffolding protein has the plurality of said cohesin domains arranged in tandem.

11. The artificial scaffolding material according to claim 9, wherein said second scaffolding protein is a cellulosome scaffolding protein.

12. The artificial scaffolding material according to claim 11, wherein said second scaffolding protein is from *Clostridium thermocellum*.

13. The artificial scaffolding material according to claim 9, wherein said cell expresses said second scaffolding protein.

14. The artificial scaffolding material according to claim 1, wherein said one or more species of proteins are enzymes.

15. The artificial scaffolding material according to claim 14, wherein said enzymes degrade cellulose.

16. The artificial scaffolding material according to claim 1, wherein said cell is a microorganism.

17. The artificial scaffolding material according to claim 16, wherein said microorganism is a eukaryotic microorganism.

18. The artificial scaffolding material according to claim 17, wherein said microorganism is an alcohol-producing yeast or an organic acid-producing yeast.

19. A protein complex material comprising:
   a cell;
   first scaffolding proteins contiguous to one another and attached to the surface of said cell, said first scaffolding proteins comprising a plurality of cohesin domains of a cellulosome arranged in tandem; and
   one or more species of proteins with compatible dockerin domains non-covalently bound to said cohesin domains,
   wherein said first scaffolding proteins are exogenous to said cell.

20. The protein complex material according to claim 19, further comprising a second scaffolding protein attached to the surface of said cell, said second scaffolding protein comprising a plurality of cohesin domains of a cellulosome,
   each of said first scaffolding proteins has a dockerin domain of a cellulosome non-covalently bound to one of said cohesin domains of said second scaffolding protein,
   wherein said second scaffolding protein is exogenous to said cell.

21. The protein complex material according to claim 20, wherein said second scaffolding protein has the plurality of said cohesin domains arranged in tandem.

22. The protein complex material according to claim 19, wherein said first scaffolding proteins include at least one first scaffolding protein having a cellulose-binding domain.

23. The protein complex material according to claim 19, wherein said one or more species of proteins are enzymes that degrade cellulose.

24. The protein complex material according to claim 23, wherein said proteins include two or more members selected from the group consisting of β-glucosidases, endoglucanases and cellobiohydrolases.

25. The protein complex material according to claim 23, wherein said cell has an ability to assimilate insoluble cellulose.

26. The protein complex material according to claim 19, wherein said cell is an alcohol-producing yeast or an organic acid-producing yeast.

27. The protein complex material according to claim 19, wherein said cell does not have the ability to produce said proteins.

28. A method of preparing a protein complex material, comprising binding proteins with compatible dockerin domains to said plurality of cohesin domains of the first scaffolding proteins of the artificial scaffolding material according to claim 1.

29. The method according to claim 28, wherein said proteins are enzymes that degrade cellulose.

30. The method according to claim 28, wherein said cell is yeast.

31. A method of degrading cellulose, comprising:
   bringing cellulose in a cellulose series material into contact with an enzyme complex material that comprises: the artificial scaffolding material according to claim 1; and one or more species of enzymes that degrade cellulose, the enzymes having compatible dockerin domains that are non-covalently bound to said plurality of cohesin domains of the first scaffolding proteins; and degrading the cellulose with said enzymes.

32. A method of producing a useful substance from cellulose, comprising:

bringing cellulose in a cellulose series material into contact with an enzyme complex material that comprises: the artificial scaffolding material according to claim 1; and one or more species of enzymes that degrade cellulose, the enzymes having compatible dockerin domains that are non-covalently bound to said plurality of cohesin domains of the first scaffolding proteins;

degrading the cellulose with said enzymes to obtain a cellulose degradation product; and assimilating and converting the cellulose degradation product into a useful substance utilizing said cell of said enzyme complex material.

33. The artificial scaffolding material according to claim 17, wherein said microorganism is yeast.

34. The artificial scaffolding material according to claim 33, wherein said microorganism is *Saccharomyces cerevisiae*.

* * * * *